US012752101B2

(12) United States Patent
Ben Yesha et al.

(10) Patent No.: US 12,752,101 B2
(45) Date of Patent: Oct. 6, 2026

(54) ELECTRICAL STIMULATION OF TISSUE

(71) Applicant: ESQURE ADVANCED MEDICAL DEVICES LTD., Shilat (IL)

(72) Inventors: Itshak Ben Yesha, Shilat (IL); Zvi Nahum, Tiberias (IL)

(73) Assignee: ESQURE ADVANCED MEDICAL DEVICES LTD., Shilat (IL)

( * ) Notice: Subject to any disclaimer, the term of this patent is extended or adjusted under 35 U.S.C. 154(b) by 486 days.

(21) Appl. No.: 17/642,062

(22) PCT Filed: Sep. 10, 2020

(86) PCT No.: PCT/IL2020/050995
§ 371 (c)(1),
(2) Date: Mar. 10, 2022

(87) PCT Pub. No.: WO2021/048854
PCT Pub. Date: Mar. 18, 2021

(65) Prior Publication Data

US 2023/0035441 A1 Feb. 2, 2023

Related U.S. Application Data

(60) Provisional application No. 62/898,602, filed on Sep. 11, 2019.

(51) Int. Cl.
*A61N 1/04* (2006.01)
*A61N 1/02* (2006.01)
*A61N 1/36* (2006.01)

(52) U.S. Cl.
CPC ........... *A61N 1/0456* (2013.01); *A61N 1/025* (2013.01); *A61N 1/0492* (2013.01); *A61N 1/36034* (2017.08)

(58) Field of Classification Search
CPC .......................... A61N 1/0456; A61N 1/36034
See application file for complete search history.

(56) References Cited

U.S. PATENT DOCUMENTS 4,541,432 A 9/1985 Molina-Negro et al.
5,723,001 A 3/1998 Pilla et al.
(Continued)

FOREIGN PATENT DOCUMENTS

AU 2017357028 A2 5/2019
EP 0111229 B1 6/1984
(Continued)

OTHER PUBLICATIONS

Murinson BB, Griffin JW. C-fiber structure varies with location in peripheral nerve. J Neuropathol Exp Neurol. Mar. 2004;63(3):246-54. doi: 10.1093/jnen/63.3.246. PMID: 15055448.
(Continued)

*Primary Examiner* — William J Levicky
(74) *Attorney, Agent, or Firm* — The Roy Gross Law Firm, LLC; Roy D. Gross

(57) ABSTRACT

A method for stimulating a group of nerves, the method comprising: placing at least one electrode in contact with skin of a subject; applying an electrical signal to the subject through the at least one electrode, wherein the electrical signal comprises a series of pulses; and continuously randomly varying at least one of the following signal parameters: (i) a duration of each of the pulses, (ii) a time interval between each pair of pulses, and (iii) an energy value of each of the pulses, while maintaining a number of pulses per second of the electrical signal above a predetermined minimum number of pulses per second, and the energy value per pulse above a predetermined minimum energy value.

14 Claims, 15 Drawing Sheets

(56) References Cited

U.S. PATENT DOCUMENTS

| | | | | |
|---|---|---|---|---|
| 2004/0267333 | A1* | 12/2004 | Kronberg | A61N 1/36021 607/72 |
| 2005/0197522 | A1 | 9/2005 | Pilla | |
| 2013/0158627 | A1 | 6/2013 | Gozani et al. | |
| 2013/0274540 | A1 | 10/2013 | Pilla | |
| 2014/0213844 | A1* | 7/2014 | Pilla | A61N 2/006 600/14 |
| 2015/0328450 | A1* | 11/2015 | Afargan | A61N 1/326 607/50 |
| 2019/0001139 | A1 | 1/2019 | Mishra et al. | |
| 2019/0217089 | A1 | 7/2019 | Bayat | |

FOREIGN PATENT DOCUMENTS

| | | | |
|---|---|---|---|
| KR | 20100089677 | A | 8/2010 |
| RU | 2441618 | C2 | 10/2011 |
| WO | 2018234964 | A1 | 12/2018 |

OTHER PUBLICATIONS

Fraccalvieri M, Salomone M, Zingarelli EM, Rivarossa F, Bruschi S. Electrical stimulation for difficult wounds: only an alternative procedure? Int Wound J. Dec. 2015;12(6):669-73. doi: 10.1111/iwj.12194. Epub Jan. 21, 2014. PMID: 24443795; PMCID: PMC7950589.

Percudani, C., Azzi, A., Bellingeri, S., Busi, S., & Afargan, M. The Use of Electrical Stochastic Noise Stimulation in the Treatment of "Hard To Heal" Wounds of Lower Limbs. 21st Conference of the European Wound Management Association, Brussels, Belgium. May 25-27, 2011.

Avrahami R, Rosenblum J, Gazes M, Rosenblum S, Litman L. The Effect of Combined Ultrasound and Electric Field Stimulation on Wound Healing in Chronic Ulcerations. Wounds. Jul. 2015;27(7):199-208. PMID: 26192738.

International Search Report of PCT/IL2020/050995 Completed Dec. 22, 2020; Mailed Dec. 23, 2020 7 pages.

Written Opinion of PCT/IL2020/050995 Completed Dec. 22, 2020; Mailed Dec. 23, 2020 4 pages.

* cited by examiner

Chart I:

ELECTRICAL STIMULATION OF TISSUE

CROSS-REFERENCE TO RELATED APPLICATIONS

This application is a National Phase of PCT Patent Application No. PCT/IL2020/050995 having International filing date of Sep. 10, 2020, which claims the benefit of priority of U.S. Provisional Patent Application No. 62/898,602 filed on Sep. 11, 2019, the contents of which are all incorporated herein by reference in their entirety.

FIELD OF THE INVENTION

Some applications of the present invention relate generally to medical devices, and more specifically to apparatus and method for electrical stimulation of tissue.

BACKGROUND

Chronic wounds are wounds that do not heal in an in a predictable amount of time and in a manner in which most wounds do. Wounds are considered chronic when wound measurements do not decrease about 10% per week or about 50% in a month.

A wound healing process is a highly orchestrated series of mechanisms where a multitude of cells and biological cascades are involved. The skin battery and current of injury mechanisms have become topics of interest for their influence in chronic wounds.

Electrical stimulation therapy assists in wound healing by affecting the electrochemical wound process. Intact skin has a transepithelial potential, with the skin surface containing a negative charge from chloride ions and the dermis maintaining a positive charge via sodium ions. Ulcerations and wounds lead to abnormalities in the transepithelial potential, and intense electrical activity measured on the skin across the wound, probably due to neural activity which may promote wound healing. Chronic wounds lose the currents and hence have decreased healing. Electrical stimulation therapy reintroduces the currents and assists with the healing process.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

In accordance with some applications of the present invention, apparatus and methods are disclosed for applying electrical stimulation therapy to a subject.

Typically, an apparatus is provided comprising an electrical stimulator comprising at least one electrode configured to be placed in contact with skin of a subject, a signal generator configured to provide an electrical signal for application to the subject through the at least one electrode, and a control processor. Optionally but not necessarily, the signal generator is configured to provide the electrical signal in an automatic non-user controllable manner.

There is thus provided, in an embodiment, an apparatus comprising an electrical stimulator comprising at least one electrode configured to be placed in contact with skin of a subject; a signal generator configured to provide an electrical signal for application to the subject through the at least one electrode, wherein the electrical signal comprises a series of pulses; and a control processor configured to continuously randomly vary at least one of the following signal parameters: (i) a duration of each of the pulses, (ii) a time interval between each pair of pulses, and (iii) an energy value of each of the pulses, while maintaining a number of pulses per second of the electrical signal above a predetermined minimum number of pulses per second, and the energy value per pulse above a predetermined minimum energy value.

There is also provided, in an embodiment, a method for stimulating a group of nerves, the method comprising: placing at least one electrode in contact with skin of a subject; applying an electrical signal to the subject through the at least one electrode, wherein the electrical signal comprises a series of pulses; and continuously randomly varying at least one of the following signal parameters: (i) a duration of each of the pulses, (ii) a time interval between each pair of pulses, and (iii) an energy value of each of the pulses, while maintaining a number of pulses per second of the electrical signal above a predetermined minimum number of pulses per second, and the energy value per pulse above a predetermined minimum energy value.

There is further provided, in an embodiment, a computer program product comprising a non-transitory computer-readable storage medium having program instructions embodied therewith, the program instructions executable by at least one hardware processor to: operate a signal generator to provide an electrical signal for application to a subject, via at least one electrode in contact with skin of the subject, wherein the electrical signal comprises a series of pulses; and continuously randomly vary at least one of the following signal parameters: (i) a duration of each of the pulses, (ii) a time interval between each pair of pulses, and (iii) an energy value of each of the pulses, while maintaining a number of pulses per second of the electrical signal above a predetermined minimum number of pulses per second, and the energy value per pulse above a predetermined minimum energy value.

In some embodiments, the duration of each of the pulses is within a predetermined duration range.

In some embodiments, the electrical signal comprises an equal number of positive polarity pulses and negative polarity pulses.

In some embodiments, a total electrical charge delivered by the electrical signal to the subject is equal to zero.

In some embodiments, the predetermined minimum number of pulses per second is 100, the predetermined minimum energy value is 0.005 microjoule, and the duration is between 0.05 ms-0.25 ms.

In some embodiments, the predetermined minimum number of pulses per second is 150, the predetermined minimum energy value is 1 microjoule, and the duration is between 0.5 ms-1 ms.

In some embodiments, the minimum number of pulses per second is 250, the minimum energy value is 0.5 microjoule, and the duration range is between 0.25 ms-0.5 ms.

In some embodiments, the predetermined minimum energy value is 2 microjoule, and said duration is between 1 ms-2.5 ms.

In some embodiments, the predetermined minimum energy value is 10 microjoule, and said duration is between 2.5 ms-10 ms.

In some embodiments, all of the signal parameters are continuously randomly being varied.

In some embodiments, the series of pulses comprises discrete pulses.

In some embodiments, the signal has a waveform selected from the group consisting of: sinusoidal, square, and triangle.

In some embodiments, a pattern of the signal parameter is repeated no more than once within a predetermined time duration. In some embodiments, the predetermined time duration is 0.2 seconds.

The electrical signal generated by the signal generator and applied to the subject is characterized by a series (train) of pulses or by a continuous waveform characterized by peaks. Typically, the pulse/peaks are characterized by at least one (e.g., at least two) parameters that are randomly varied by the control processor during application of the signal. Additionally, the control processor is configured to provide the signal such that a pre-determined energy dose is applied to the subject by the signal despite the varying pulse/peak parameters.

For some applications, the at least two pulse/peak parameters comprise a pulse/peak duration and a pulse/peak energy level which are each randomly varied, independently of each other (and independently of the energy dose applied to the subject by the signal), by the control processor during application of the signal. It is noted that although the pulse/peak parameters are randomly varied independently of each other, the variation of one parameter may influence one or more other parameters. For example, increasing a pulse/peak duration may increase the energy level applied by the pulse/peak. It is further noted that additional pulse/peak parameters (e.g., Volt/Watt amplitude, and frequency) may also be randomly varied by the control processor. Additionally, or alternatively, in cases in which the electrical signal is a pulsed signal, the control processor is configured to randomly vary the intervals between the pulses such that the pulses and in particular identical pulses, are applied at random intervals during application of the signal.

For some applications, the signal generator is configured to generate at least one waveform or train of pulses. For example, the signal generator is configured to generated at least first and second waveforms or train of pulses. The waveforms may contain any known type of waveform, e.g. a sine wave, a square wave, a triangle wave and/or a sawtooth wave, or any other type of waveform. The first and second waveforms or train of pulses are each characterized by a series of a minimum number of positive and negative pulse/peaks that are applied per second (typically, the first and second waveforms or train of pulses having a different number of minimum pulse/peaks). Additionally, the pulse/peaks of each waveform are characterized by varying energy levels having a minimum and maximum microjoule range, and varying pulse/peak durations having a minimum and maximum pulse/peak duration range. Further additionally, an average energy that is applied by the waveforms or train of pulses varies between the first and second waveforms or train of pulses.

The control processor is configured to randomly mix the series of pulse/peaks within each of the waveforms or train of pulses and between the waveforms or train of pulses to provide a randomly mixed series of pulse/peaks such that the electrical signal that is applied to the subject through the at least one electrode comprises pulse/peaks having varied and random energy levels and duration. For some applications, the pulse/peaks are additionally applied at random intervals to the subject by the at least one electrode of the electrical stimulator.

The control processor is further configured to mix the series of positive and negative polarity pulse/peaks such that a pulse/peak with positive polarity is followed by a pulse/peak with negative polarity (and vice versa), thereby ensuring safety of the apparatus by balancing the electrical charge and reducing buildup of an electrical charge.

Optionally but not necessarily, when the signal is a pulsed signal, the control processor is configured to mix the pulses such that a random and changing interval (time gap) exists between the negative and positive pulses. During the time gap between the negative and positive pulses, there is typically no current flow such that each pulse is an isolated electrical event. For other applications, uniform intervals exist between the pulses. Additionally, for some applications the electrical signal is applied as a continuous signal with no intervals.

For some applications, the control processor is configured to mix the series of pulse/peaks such that a parameter pattern (e.g., a combination of energy levels and duration of pulse/peaks) of the series of pulse/peaks that is applied during a pre-determined subset of a duration of the signal, is not repeated within the same subset, thereby further contributing to the variation of the signal. For example, a parameter pattern is not repeated within a pre-determined subset time frame of 0.2 seconds. However, despite the random combination of pulse/peak parameters, a pre-determined energy dose is applied to the subject by the signal.

For some applications, the electrical signal is applied to the subject for a treatment therapy session of at least 10 minutes a day, and typically between 20-30 minutes 2-3 times a day. For some applications, the at least one electrode is placed in contact with intact skin anywhere on the subject's body. For some applications, the electrical stimulation therapy is applied to a subject suffering from a chronic wound. Optionally but not necessarily, if the subject suffers from a chronic wound, the electrode is placed in a vicinity of the wound. Alternatively, if the subject suffers from a chronic wound, the electrode is placed at a distance from the wound, e.g., more than 100 cm from the wound.

In accordance with some applications of the present invention, the electrical stimulation therapy applied by the apparatus, assists in chronic wound healing and/or revascularization and oxygen perfusion in the body. Additionally, or alternatively, the electrical stimulation therapy applied by the apparatus in accordance with some applications of the present invention, promotes growth of granulation tissue and epithelialization.

It is hypothesized by the inventors that applying a random and varying electrical signal having the characteristics described herein, facilitates enhanced wound healing, blood vessel formation, and revascularization compared to other known electrical therapy stimulation procedures. The inventors hypothesize that applying the varied mixed electrical signal characterized herein prevents the body from adapting to the applied electrical stimulation, thereby achieving better wound healing and revascularization parameters. Additionally, or alternatively, it is hypothesized by the inventors that application of the varied mixed electrical signal characterized herein facilitates stimulation of different nerve groups at different depth levels, thereby achieving enhanced wound healing and revascularization parameters.

Additionally, or alternatively, it is hypothesized by the inventors that application of a random and varying electrical signal as characterized herein, particularly plays a role in stimulation of unmyelinated Group C afferent fibers. The varied electrical signal applied to the Group C afferent fibers nerve, in accordance with some applications of the present invention, signals the existence of an injury to the CNS, hence activating the delivery of "repair" orders in the efferent nerves, and thereby achieving enhanced wound healing and revascularization parameters.

There is therefore provided in accordance with some applications of the present invention, apparatus including: an electrical stimulator including at least one electrode configured to be placed in contact with skin of a subject; and a signal generator configured to provide electrical signal for application to the subject through the at least one electrode, the electrical signal characterized by a series of pulses or peaks of a wave; and a control processor configured to (i) randomly vary at least one parameter of the pulse or peak parameters during application of the signal and (ii) provide the signal such that a pre-determined energy dose is applied to the subject by the signal independently of the randomly varied pulse or peak parameters.

For some applications, the control processor is configured to randomly vary at least two pulse/peak parameters.

For some applications, the control processor is configured to randomly vary a plurality of pulse/peak parameters.

For some applications, the control processor is configured to randomly vary a plurality of combinations of pulse/peak parameters.

For some applications, the control processor is configured to randomly vary the pulse/peak parameters independently of each other.

For some applications, the at least one pulse/peak parameter includes a pulse/peak duration range and the control processor is configured to randomly vary the duration range of the pulse/peaks during the signal.

For some applications, the pulse/peak duration includes at least two different pulse/peak durations, a first pulse/peak duration having a first minimum and maximum duration range and a second pulse/peak duration having a different second minimum and maximum duration range.

For some applications, one of the at least two pulse/peak parameters include an energy range level of the pulse/peak and the control processor is configured to randomly vary the energy range level of the pulse/peaks during the signal.

For some applications, the varying energy level parameters include at least two different energy levels, a first energy level having a first minimum and maximum microjoule range and a second energy level having a different second minimum and maximum microjoule range.

For some applications, the first energy level has first average energy having a first average minimum and maximum microjoule range, and the second energy level has second average energy having a second average minimum and maximum microjoule range.

For some applications, a parameter pattern of the series of pulse/peaks that is applied during the signal, is not repeated within a pre-determined time frame subset within the signal.

For some applications, the parameter pattern is not repeated in a pre-determined time frame subset of 0.2 seconds.

For some applications, the varying energy level parameters include at least two different energy levels, a first energy level having a first minimum and maximum microjoule range and a second energy level having a different second minimum and maximum microjoule range.

For some applications, the first energy level has first average energy having a first average minimum and maximum microjoule range, and the second energy level has second average energy having a second average minimum and maximum microjoule range.

For some applications, the control processor is configured to randomly vary a duration of intervals between the pulses such that the series of pulse are applied at random intervals between the pulses during the signal.

For some applications, the random intervals include at least two different interval durations.

For some applications, the pre-determined energy dose includes a maximum energy level of 15 volt.

For some applications, the signal generator is configured to provide the electrical signal as an automatic non-user-controllable signal.

For some applications, the electrical signal is a stochastic AC signal.

For some applications, the at least one electrode includes at least two electrodes.

For some applications, the at least one electrode is placed in contact with intact skin of the subject.

For some applications, the at least one electrode is placed in contact with skin of the subject in the vicinity of a wound in the skin.

For some applications, the at least one electrode includes at least two electrodes, and the at least two electrodes configured to be placed on two opposing sides of a wound in the skin.

For some applications, the at least one electrode is placed in contact with skin of the subject in a location suffering from impaired oxygenation.

For some applications, the at least one electrode is placed upstream of afferent axons leading to the spinal cord.

For some applications, the peaks include varying waveforms selected from the group consisting of: sinusoidal, square, or triangle waveforms.

For some applications, the series of pulse/peaks includes a series of pulse/peaks in which a positive pulse/peak is followed by a negative pulse/peak and a negative pulse/peak is followed by a positive pulse/peak.

There is therefore provided in accordance with some applications of the present invention, a method for stimulating a first group of nerves at a first tissue depth, the method including: placing at least one electrode in contact with skin of a subject; applying an electrical signal to the subject through the at least one electrode, the electrical signal being characterized by a series of pulse or peaks of a wave; randomly varying at least one parameter of the pulses/peaks; applying, independently of the randomly varying the pulse/peak parameters, a first pre-determined dose of energy by applying the electrical signal to the subject, thereby stimulating the first group of nerves at the first tissue depth.

For some applications, the method further includes applying independently of randomly varying the pulse/peak parameters, a second pre-determined dose of energy to the subject by application of the signal and stimulating a second group of nerves at a second tissue depth, the first tissue depth being different than the second tissue depth.

For some applications, the method further includes randomly selecting the first and second groups of nerves to be stimulated.

For some applications, the method further includes randomly varying intervals between the pulses.

For some applications, the method further includes controlling application of the series of pulse/peaks such that a parameter pattern of the series of pulse/peaks that is applied during a time frame subset of the electrical signal, is not repeated during the same subset.

For some applications, placing the at least one electrode includes placing at least two electrodes.

For some applications, placing the at least one electrode includes placing at least two electrodes on opposing sides of a wound in the skin.

For some applications, placing the at least one electrode includes placing the electrode in the vicinity of a wound in the skin.

For some applications, placing the at least one electrode includes placing the electrode at least 5 cm from an outermost edge of the wound.

For some applications, the method further includes promoting healing of a wound in the skin of the subject by applying the electrical signal.

For some applications, the method further includes reducing pain in the subject by applying the electrical signal.

For some applications, the method further includes increasing revascularization in the subject by applying the electrical signal.

For some applications, the method further includes increasing granulation in the skin of the subject by applying the electrical signal.

For some applications, the method further includes increasing oxygen perfusion in the subject by applying the electrical signal.

For some applications, the method further includes decreasing healing time of a wound in the skin.

For some applications, applying the electrical signal includes applying the electrical signal for a duration of 10-30 minutes 1-3 times within 24 hours.

For some applications, the method further includes generating the electrical signal in an automatic non-user controllable manner.

There is therefore provided in accordance with some applications of the present invention, a computer program product including a non-transitory computer-readable storage medium having program code embodied therewith, the program code executable by at least one hardware processor to: generate via at least one electrode in contact with skin of a subject an automatic non-user controllable an electrical signal characterized by a series of pulses or peaks of a wave applied at randomly varying pulse/peak parameters; apply, independently of the randomly varying pulse/peak parameters, a first pre-determined dose of energy to the subject by application of the signal; and stimulate a first group of nerves at first tissue depth.

For some applications, the computer program product further includes applying the pulses at random intervals.

There is therefore provided in accordance with some applications of the present invention, apparatus including: a signal generator configured to generate an electrical signal characterized by: a first series of pulses or peaks of a wave including a series of at least 250 positive current pulse/peaks and at least 250 negative current pulse/peaks per second, having (i) an energy level of 0.5-13 microjoule, (ii) a pulse/peak duration of 0.25 ms-0.5 ms and (iii) an average energy of 1-4 microjoule; a second series of pulses or peaks of a wave including a series of at least 100 positive current pulse/peaks and at least 100 negative current pulse/peaks per second, having (i) an energy level of 0.005-7 microjoule, (ii) a pulse/peak duration of 0.05 ms-0.25 ms and (iii) an average energy of 0.02-1 microjoule; a control processor electrically coupled to the signal generator and configured to mix the series of pulse/peaks of the first and second series of pulses or peaks of a wave; an electrical stimulator including at least one electrode configured to be placed in contact with skin of a subject to apply the mixed pulse/peaks at random intervals between the pulse/peaks to the subject.

For some applications, the signal generator is further configured to generate a third series of pulses or peaks of a wave including a series of at least 150 positive current pulse/peaks and at least 150 negative current pulse/peaks per second, having (i) an energy level of 1-20 microjoules, (ii) a pulse/peak duration of 0.5 ms-1 ms and (iii) an average energy of 2-10 microjoule; and the control processor is configured to mix the series of pulse/peaks of the first, second and third series of pulses or peaks of a wave.

For some applications, the signal generator is further configured to generate a fourth series of pulses or peaks of a wave including a series of at least 30 positive current pulse/peaks and at least 30 negative current pulse/peaks per second, having (i) an energy level of 2-40 microjoules, (ii) a pulse/peak duration of 1 ms-2.5 ms and (iii) an average energy of 4-20 microjoule; and the control processor is configured to mix the series of pulse/peaks of the first, second, third and fourth series of pulses or peaks of a wave.

For some applications, the signal generator is further configured to generate a fifth series of pulses or peaks of a wave including a series of at least 0.5 positive current pulse/peaks and at least 0.5 negative current pulse/peaks per second, having (i) an energy level of 10-250 microjoules, (ii) a pulse/peak duration of 2.5 ms-10 ms and (iii) an average energy of 20-200 microjoule; and the control processor is configured to mix the series of pulse/peaks of the first, second, third, fourth and fifth series of pulses or peaks of a wave.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
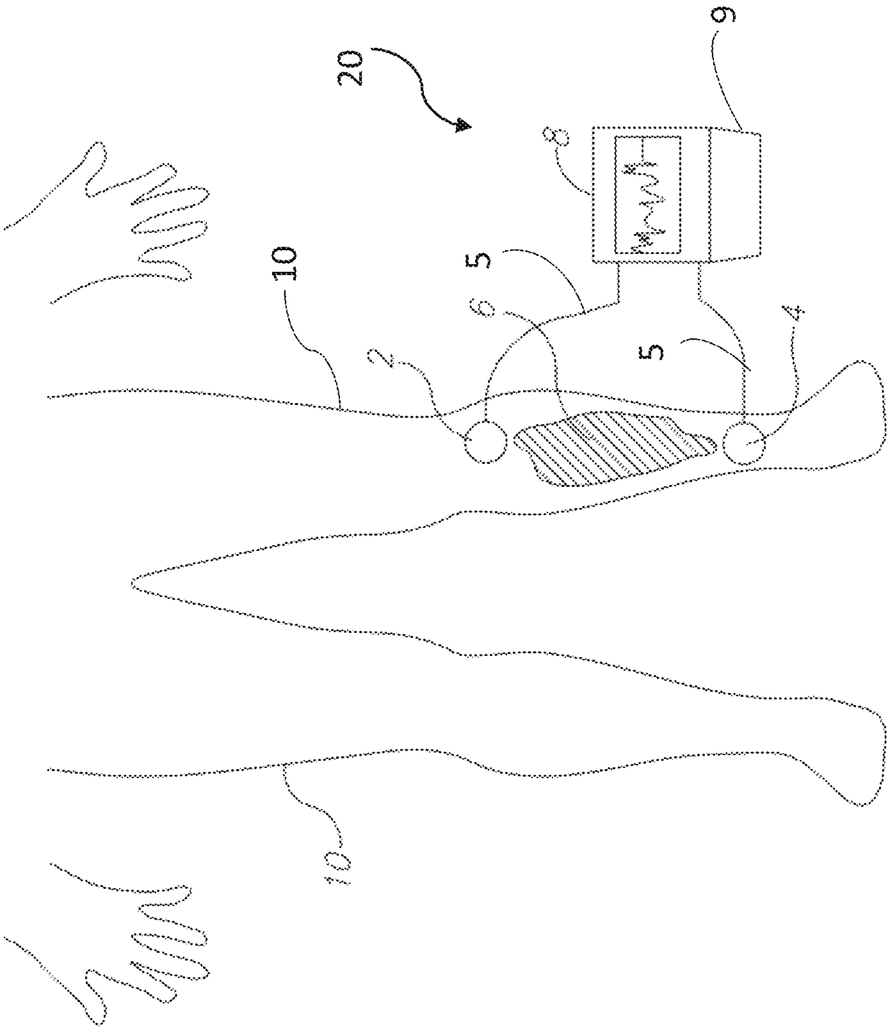
FIG. 1 is a schematic illustration of apparatus for application of electrical stimulation therapy comprising electrodes placed on skin of a subject in the vicinity of a wound, in accordance with some applications of the present invention.

In some aspects of the present invention, apparatus is provided for applying electrical stimulation therapy to a subject. Optionally but not necessarily, the electrical stimulation that is applied in accordance with some applications of the present invention, accelerates and improves wound healing, increases revascularization, promotes blood flow and improves circulation and oxygen levels in tissue.

In accordance with some aspects of the present invention, the electrical stimulation applied to the subject comprises an electrical signal of pulsed electrical current or a waveform characterized by peaks of the wave in which operating parameters (e.g., energy levels, number of pulse/peaks per seconds, wave forms, pulse/peak patterns and/or pulse/peak duration) of the pulse/peaks are varied randomly and continuously over the course of the pulse/peaks. Thereby, providing the subject with a randomly changing electrical signal delivering a total of a pre-determined dose electrical energy by the signal (despite the varying pulse/peak parameters). In general, a pre-determined positive dose of energy is delivered to the subject, however, the total electrical charge that is applied to the subject over a treatment session is practically zero.

In accordance with some aspects of the present invention, the electrical stimulation is applied by apparatus comprising an electrical stimulator having at least one electrode (e.g., two electrodes) configured to be placed in contact with skin of a subject. The apparatus further comprises a signal generator configured to provide the electrical signal through the at least one electrode. Optionally but not necessarily, the signal generator configured to provide the electrical signal in an automatic and non-user-controllable manner. For some applications the signal generator comprises a power source and is configured to generate at least one series of pulses/waveforms. Typically, the signal generator generates a first and second series of pulses/waveforms. The waveforms may be any known type of waveform, e.g. a sine wave, a square wave, a triangle wave and/or a sawtooth wave or a combination thereof. The apparatus further comprises a control processor configured to randomly vary the pulse/peaks to provide the subject with the randomly changing electrical signal. Typically, the electrical current applied in accordance with some applications of the present invention, is characterized by randomly varying pulse/peak parameters such as number of pulse/peaks per second, duration, and pulse/peak energy level.

Additionally, the pulse/peaks are typically applied as a train of positive and negative polarity pulse/peaks, in which a positive polarity pulse/peak is followed by a negative polarity pulse/peak (or vice versa).

Optionally but not necessarily, in the case of pulsed current, a random and changing interval (time gap) exists between the negative and positive pulses. During the time gap between the negative and positive pulse/peaks, there is no current flow such that each pulse is an isolated electrical event.

Reference is now made to FIG. 1, which is a schematic illustration of apparatus 20 for application of electrical stimulation therapy to a subject, in accordance with some applications of the present invention. Apparatus 20 typically comprises a signal generator 8, an electrical stimulator comprising electrodes 2 and 4 configured to be placed in contact with skin of the subject, and control processor 9. When apparatus 20 is operated, an electrical current is generated by signal generator 8 and passed through electrodes 2 and 4 to the subject. The electrical current is typically a treatment signal waveform comprising a train of pulse/peaks. Apparatus 20 may further include an amplifier (not shown), and/or a power source (not shown), and/or the like. Control processor 9 may be an analog signal processor or a digital signal processor. For example, electrical signal generator 8 is a digital signal generator operated by at least one hardware processor to produce the signal output from a preamplifier. For example, the amplifier is a current limited digital voltage amplifier, such as an electronic device that increases the power of a signal from the electrical signal generator. For example, a power source is an alkaline battery, a lead-acid battery, a rechargeable lithium-ion battery, a nickel metal hydride battery, and/or the like.

Signal generator 8 typically generates the electrical signal for providing treatment to the subject for improving oxygen perfusion in the subject to facilitate healing of chronic wound 6. The electrical signal is passed to electrodes 2 and 4 which are placed in contact with the skin of the subject to deliver the treatment signal waveform electrical current anywhere on the body of the subject. Electrode 2 and 4 are typically configured to be placed in contact with intact skin of a subject. For some applications, as shown in FIG. 1, apparatus 20 comprises two electrodes 2 and 4 which are placed in contact with skin of the subject. It is noted that apparatus 20 may comprise more than two electrodes. Apparatus 20 typically further comprises a signal generator 8 and a control processor 9.

Optionally, signal generator 8 provides an automatic non-user-controllable electrical signal for application to the subject through at least one electrode 2 and/or 4 (optionally through electrical leads 5). The electrical signal applied by signal generator 8 is typically characterized by a series of pulse/peaks having at least two pulse/peak parameters (e.g., a pulse/peak duration and a pulse/peak energy level) that are randomly varied during application of the signal. In accordance with some application of the present invention, control processor 9 is configured to (i) randomly vary each one of the pulse/peak parameters during application of the electrical signal and (ii) provide the electrical signal such that a pre-determined total dose of energy, is applied to the subject by the signal, regardless and independently of the varied pulse/peak parameters. Typically, the pulse/peak parameters are randomly varied continuously for the duration of the signal. The pulse/peak parameters are typically varied independently of each other.

Electrodes 2 and 4 are shown in FIG. 1 as being positioned in the vicinity of wound 6 and in particular on opposing sides of wound 6, by way of illustration and not limitation. It is noted that, in accordance with some applications of the present invention, electrodes 2 and 4 may be placed anywhere on the subject's skin or on an article wore by the subject (as described elsewhere herein).

For some applications, control processor 9 is configured to mix the series of pulse/peaks such that a parameter pattern (e.g., a combination of energy levels and duration of pulse/peaks) of the series of pulse/peaks that is applied during a pre-determined subset of a duration of the signal, is not repeated within the same subset, thereby further contributing to the variation of the signal. For example, a parameter pattern is not repeated within a pre-determined subset time frame of 0.2 seconds. However, despite the random combination of pulse/peak parameters, a pre-determined dose of energy is applied to the subject by application of the signal.

For example, the pre-determined dose of energy comprises a maximum electrical potential level of 15 volt.

For some applications, signal generator 8 is configured to generate at least one waveform or a train of pulses. For example, signal generator 8 is configured to generate at least first and second waveforms or train of pulses. The first and second waveforms (or train of pulses) are each characterized by a series of a minimum number of positive and negative pulse/peaks that are applied per second (typically, the first and second waveforms having a different number of minimum pulse/peaks). Additionally, the pulse/peaks of each waveform are characterized by varying energy levels having a minimum and maximum microjoule range, varying pulse/peak durations having a minimum and maximum pulse/peak duration range. Further additionally an average energy that is applied by the waveforms varies between the first and second waveforms.

For example, the first waveform (or train of pulses) is characterized by a series of at least 250 positive current pulse/peaks and at least 250 negative current pulse/peaks per second, having an energy level in a range of 0.5-13 microjoule, a pulse/peak duration of 0.25 ms-0.5 ms and an average energy of 1-4 microjoule. The second waveform is characterized by a series of at least 100 positive current pulse/peaks and at least 100 negative current pulse/peaks per second, having an energy level in a range of 0.005-7 microjoule, a pulse/peak duration of 0.05 ms-0.25 ms, and an average energy of 0.02-1 microjoule.

For some applications, the signal generator is configured to generate additional waveforms (or train of pulses) characterized by having a different number of minimum pulse/peaks and the pulse/peaks having varying energy levels with a minimum and maximum microjoule range, varying pulse/peak durations with a minimum and maximum pulse/peak duration range, and an average energy level.

For example, the signal generator generates a third waveform (or train of pulses) characterized by a series of at least 150 positive current pulse/peaks and at least 150 negative current pulse/peaks per second, having an energy level in a range of 1-20 microjoules, a pulse/peak duration of 0.5 ms-1 ms and an average energy of 2-10 microjoule.

Additionally, or alternatively, the signal generator generates a fourth waveform (or train of pulses) characterized by a series of at least 30 positive current pulse/peaks and at least 30 negative current pulse/peaks per second, having an energy level in range of 2-40 microjoules, a pulse/peak duration of 1 ms-2.5 ms and an average energy of 4-20 microjoule.

Further additionally, or alternatively, the signal generator generates a fifth waveform (or train of pulses) characterized by a series of at least 0.5 positive current pulse/peaks and at least 0.5 negative current pulse/peaks per second, having an energy level of 10-250 microjoules, a pulse/peak duration of 2.5 ms-10 ms and an average energy of 20-200 microjoule.

Typically, control processor 9 is configured to randomly mix the series of pulse/peaks within each of the waveforms (or train of pulses) and between the waveforms (or train of pulses) to provide a randomly mixed series of pulse/peaks such that the electrical signal that is applied to the subject through the at least one electrode comprises pulse/peaks having varied and random energy levels and duration. Additionally, the pulses may be applied at random intervals to the subject by the at least one electrode of the electrical stimulator.

Typically, despite the randomly applied electrical signal and various combinations of pulse/peak parameters, a pre-determined dose of energy is applied to the subject by the signal. Additionally, the control processor is configured to mix the series of pulse/peaks such that a parameter pattern (e.g., energy levels and duration of pulse/peaks) of the series of pulse/peaks that is applied during a pre-determined time frame subset of the signal, is not repeated within the same subset, further contributing to the variation of the signal.

Figure 2:
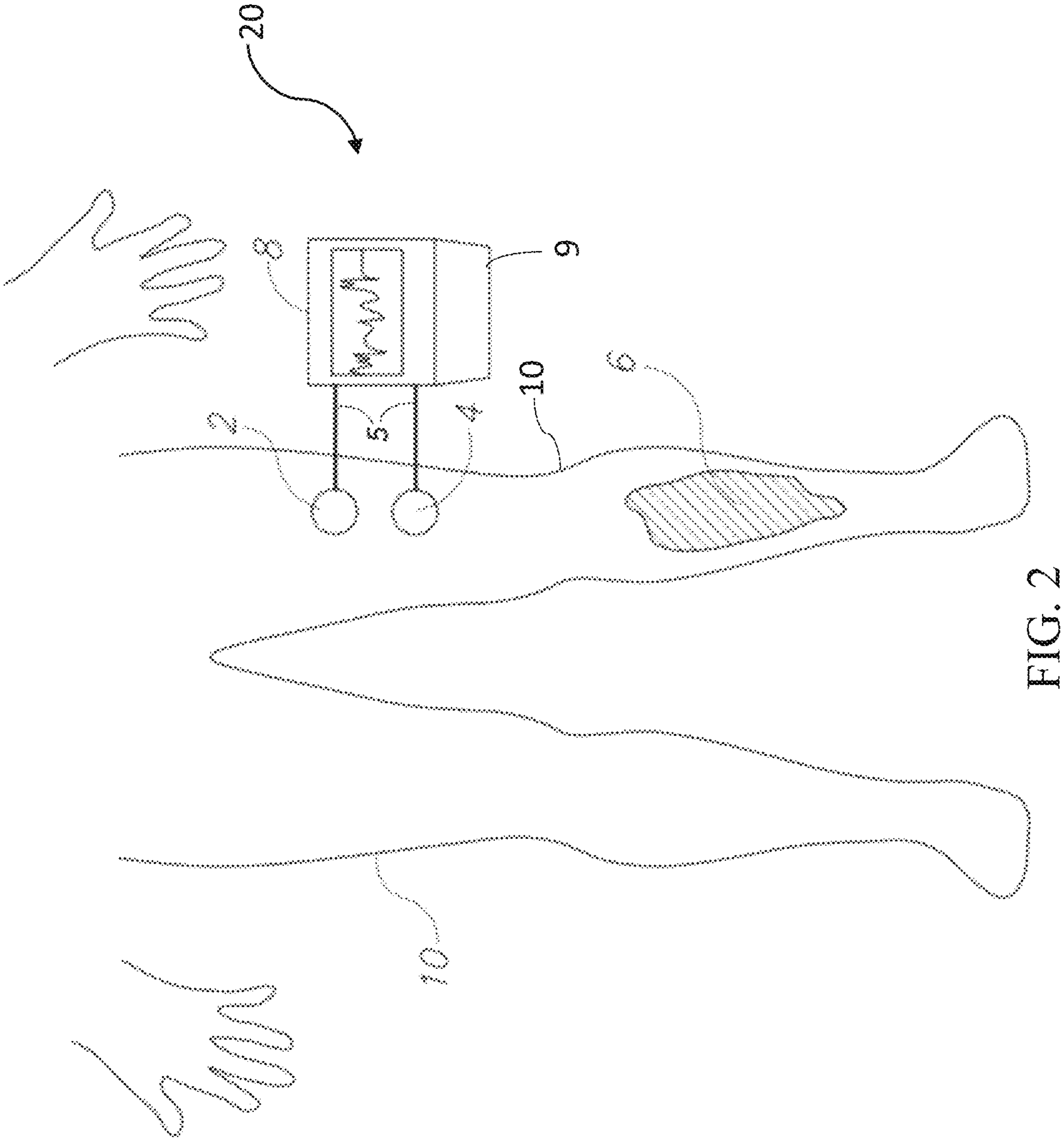
FIG. 2 is a schematic illustration of apparatus for application of electrical stimulation therapy comprising electrodes placed on skin of a subject distant from a wound, in accordance with some applications of the present invention.

Reference is now made to FIG. 2, which is a schematic illustration of apparatus 20 for application of electrical stimulation therapy comprising electrodes 2 and 4 placed on skin 10 of the subject distant from wound 6, in accordance with some applications of the present invention. As described with reference to FIG. 1, signal generator 8 is electrically connected to two or more electrical leads 5. For example, electrical leads 5 are electrically connected to two electrodes, 2 and 4, which are electrically connected to skin 10 of a patient.

For some applications, electrodes 2 and 4 are positioned at least 5 centimeters distant from the anatomical location of a wound 6 as measured along the surface of the skin between the closest edge of the wound to the nearest electrode. For example, the treatment of a wound on the foot is performed with electrodes connected to the thigh 45 centimeters from the wound. For example, treatment of a wound on the thigh is performed with electrodes connected to a wristband 110 centimeters from the wound along the skin surface. For example, treatment of a wound on the calf is performed with electrodes connected to the thigh 20 centimeters from the wound. Electrodes 2 and 4 may be placed at a distance away from wound 6, such as anywhere on the body. For example, the electrodes may be placed on a wrist strap device, a waist belt, a wristwatch, an upper arm strap device, a head strap device, eyeglasses, an article of clothing, a clothing accessory, and/or the like. For example, in a wrist or upper arm strap device the electrodes are placed in the strap with exposed electrical contacts, such as electrodes, on the side of the strap closest to the skin and the electrical signal generator is placed embedded within the strap. For example, in eyeglasses the electrodes are placed on the arms with the electrodes posed on the sides touching the skin above the ears and the electrical signal generator inside the frame. For example, in a hat the electrodes are placed in an internal hat band with electrical contact exposure to the temples and an electrical signal generator within the hat frame. As another example, the signal generator 8 and electrodes 2 and 4 may be incorporated into exercise equipment such as a handle, an electronic device such as a television controller, household equipment such as a broom handle, a mop handle, and/or the like.

Figure 3:
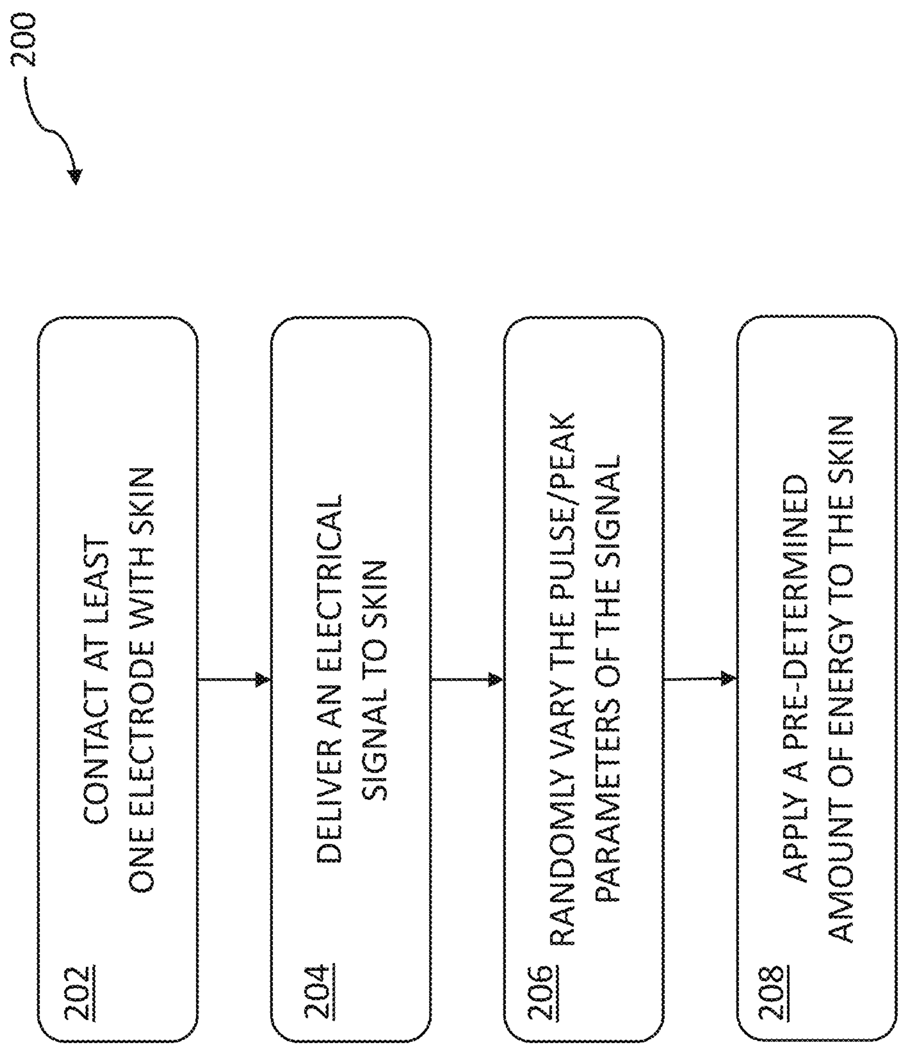
FIG. 3 is a flowchart illustrating a method for treating a subject by application of electrical stimulation therapy, in accordance with some applications of the present invention.

Reference is now made to FIG. 3 which is a flowchart illustrating a method for treating a subject by application of electrical stimulation therapy, in accordance with some applications of the present invention. Typically, at least one electrode is positioned in contact with skin of the subject (202) such that the electrical stimulation is applied to the subject through the electrodes. Typically, the electrical stimulation is applied to the subject as an electrical signal (204) characterized by a train of pulse/peaks having pulse/peak parameters such as a pulse/peak duration and a pulse/peak energy level. The pulse/peak parameters are randomly varied, independently of each other, throughout the duration of the signal application (206) to yield an electrical signal characterized by randomly varying pulse/peak parameters. For some applications, the series of pulse/peaks are mixed such that a parameter pattern (e.g., a combination of energy levels and duration of pulse/peaks) of the series of pulse/peaks that is applied during a pre-determined subset of a duration of the signal, is not repeated within the same subset, thereby further contributing to the variation of the signal. For example, a parameter pattern is not repeated within a pre-determined subset time frame of 0.2 seconds. However, despite the random combination of pulse/peak parameters, a pre-determined dose of energy is applied to the subject by application of the signal (208). For example, the pre-determined dose of energy comprises a maximum energy level of 15 volt.

For some applications, the electrical stimulation therapy (i.e., the electrical signal) is applied to the subject for at least 10 minutes a day; and typically between 20-30 minutes 2-3 times a day. For some applications, the electrical stimulation therapy is applied to a subject suffering from a chronic wound. For some such applications, the electrodes are positioned in contact with skin in the vicinity of the wound. Additionally, or alternatively, the electrodes are positioned in contact with skin that is distant from the wound.

For some applications, the electrical stimulation therapy (i.e., the electrical signal) application protocol, for example, the duration of the treatment, the frequency of treatments and time interval between treatments may vary e.g., in accordance with the characteristics of the wound and tissue to be treated. For example, for some applications, the electrical stimulation therapy (i.e., the electrical signal) is applied to the subject for at least 10 minutes a day, and typically between 20-30 minutes 2-3 times a day. For some applications, the electrical stimulation therapy is applied to a subject suffering from a chronic wound. For some such applications, the electrodes are positioned in contact with skin in the vicinity of the wound. Additionally, or alternatively, the electrodes are positioned in contact with skin that is distant from the wound.

In accordance with some applications of the present invention, the electrical stimulation therapy applied by the apparatus, assists in chronic wound healing and/or revascularization and oxygen perfusion in the body. Additionally, or alternatively, the electrical stimulation therapy applied by the apparatus in accordance with some applications of the present invention, promotes growth of granulation tissue and epithelialization.

An established theory states that wound healing causes a short circuit, such as a lower resistance, of this electrophysiological process, current flows from back from the subdermal skin layers to the outer surface of the wound, an electrical field is generated from this current, and the electrical field draws in tissue repairing cells. Thus, the current scientific theory defines this process as a local process, such as a paracrine signaling process. In chronic wounds, this process is interrupted, and the healing is either slowed or stopped, preventing the healing of the wound. According to this theory, electrostimulation for wound healing generates an artificial electrical field that stimulates healing of the wound.

Further with regard to chronic wounds, the inventors hypothesize that wounds require a healthy level of tissue oxygenation for promoting granulation and epithelization required for healing. However, in cases of chronic wounds, occurrence of the wound causes an oxygen deficiency in the wound as well as nerve damage (e.g., damage to dendrites and axons of the neurons). This nerve damage over time causes impaired signaling, consequently leading to impaired wound healing. Electrostimulation breaks this cycle by reinitiating the appropriate signal transduction leading to resuming of the healing process. For example, the electrical signal initiates a signal stimulating healing by signaling a message reporting disintegration of nerves up the nerve system. The delivery of the electrical signal anywhere on the body of a subject signals the brain of the subject to treat wounds on the body, in particular in cases of a chronic wound.

It is further hypothesized by the inventors that applying a random and varying electrical signal having the characteristics described herein, facilitates enhanced wound healing and revascularization compared to other known electrical therapy stimulation procedures. The inventors hypothesize that applying the varied mixed electrical signal characterized herein prevents the body from adapting to the applied electrical stimulation, thereby achieving better wound healing and revascularization parameters. Additionally, or alternatively, it is hypothesized by the inventors that application of the varied mixed electrical signal characterized herein facilitates stimulation of different nerve groups at different depth levels, thereby achieving enhanced wound healing and revascularization parameters.

Experimental Data

The experiments described hereinbelow were performed by the inventors in accordance with applications of the present invention and using the apparatus and techniques described herein. The experiments presented hereinbelow with reference to Examples 1-2 demonstrate that application of the electrical signal in accordance with the apparatus and techniques described herein, can be used for accelerating and improving wound healing, as well as improving tissue oxygenation.

Example 1

In a set of experiments, the effect of the apparatus and techniques described herein on chronic wound healing was examined.

Methods in Example 1

A series of protocols are described hereinbelow which may be used separately or in combination, as appropriate, in accordance with applications of the present invention. It is to be appreciated that numerical values are provided by way of illustration and not limitation. Typically, but not necessarily, each value shown is an example selected from a range of values that is within 10% of the value shown. Similarly, although certain steps are described with a high level of specificity, a person of ordinary skill in the art will appreciate that other steps may be performed, mutatis mutandis.

In accordance with some applications of the present invention, the following methods were applied:

Obtaining Subject Population

IRB approval (Clalit Health Services, Tel Aviv, Israel) was received to perform a retrospective analysis of patients treated with the apparatus and techniques described herein.

The subject population included subjects (N=29) presented with a total of 34 Diabetic Foot Ulcers or Venous Leg Ulcers. To be included in the study, patients must have had a wound that was present for a minimum of 3 months, and which failed to improve for a minimum period of 30 days prior to enrollment, as assessed by a physician. Patients enrolled in the study were given instruction as to the proper use of the apparatus and were instructed to use it three times daily for thirty minutes each session. A total of 34 wounds were presented in the 29 patients. 18 of the wounds were in male subjects, and 16 of the wounds were in female subjects. 22 wounds were Diabetic Foot Ulcers and 12 wounds were Venous Leg Ulcers. The average age of the subjects enrolled was 77.2 years. The average duration of wounds at presentation was 7.5 months. The average size of the wounds at presentation was 4.08 $cm^2$ (Range 0.15-21.02).

Information for the 29 subjects (and 34 wounds) is as set forth in the following Table A:

TABLE A

| Wound Type | Gender | Patient Age (years) | Wound duration (months) | Days to heal | At Presentation ($cm^2$) | At 4 Weeks ($cm^2$) | At 12 Weeks ($cm^2$) |
|---|---|---|---|---|---|---|---|
| Diabetic | M | 65 | 12 | * | 0.66 | 0.03 | 0.01 |
| Diabetic | F | 56 | 5 | * | 1.96 | 2.10 | 2.00 |
| Venous | M | 86 | 3 | 30 | 0.72 | 0.00 | ** |
| Venous | M | 70 | 3 | * | 1.58 | 0.88 | 1.02 |
| Venous | M | 70 | 3 | 137 | 0.70 | 0.36 | 0.21 |
| Diabetic | F | 84 | 3 | * | 3.56 | 2.90 | 1.46 |
| Diabetic | M | 88 | 8 | * | 1.51 | 1.38 | 1.39 |
| Venous | F | 84 | 12 | 70 | 4.80 | 2.99 | 0.00 |
| Diabetic | F | 68 | 3 | 133 | 1.02 | 1.00 | 0.31 |
| Venous | F | 62 | 6 | 70 | 1.19 | 0.48 | 0.00 |
| Venous | F | 89 | 3 | 104 | 15.76 | 5.89 | 0.64 |
| Venous | F | 92 | 17 | 63 | 14.79 | 3.87 | 0.00 |
| Venous | M | 70 | 20 | * | 6.78 | 2.62 | 1.62 |
| Diabetic | M | 67 | 8 | * | 11.74 | 5.53 | 1.44 |
| Diabetic | M | 75 | 3 | 140 | 6.82 | 5.10 | 1.87 |
| Diabetic | M | 64 | 3 | 84 | 2.25 | 1.70 | 0.00 |
| Diabetic | M | 66 | 6 | 72 | 0.86 | 0.18 | 0.00 |
| Diabetic | M | 70 | 9 | 70 | 0.11 | 0.10 | 0.00 |
| Diabetic | F | 81 | 3 | 75 | 1.46 | 0.91 | 0.00 |
| Diabetic | F | 77 | 12 | 63 | 0.76 | 0.15 | 0.00 |
| Diabetic | M | 65 | 12 | 39 | 0.15 | 0.00 | ** |
| Diabetic | F | 92 | 3 | 108 | 6.43 | 6.09 | 0.89 |
| Diabetic | F | 94 | 4 | 58 | 0.21 | 0.00 | ** |
| Venous | M | 80 | 3 | 27 | 2.17 | 0.00 | ** |
| Diabetic | M | 87 | 7 | * | 21.02 | 13.76 | 18.12 |
| Diabetic | M | 86 | 12 | * | 6.22 | 6.44 | 1.54 |
| Diabetic | M | 65 | 12 | 112 | 0.55 | 0.43 | 0.05 |
| Venous | F | 70 | 12 | 45 | 15.40 | 10.00 | 0.00 |
| Venous | F | 94 | 7 | 50 | 0.62 | 0.32 | 0.00 |
| Diabetic | F | 74 | 12 | 56 | 0.49 | 0.47 | 0.00 |
| Diabetic | F | 65 | 12 | 126 | 1.08 | 1.27 | 0.44 |
| Diabetic | M | 76 | 3 | * | 3.31 | 3.31 | 1.79 |
| Venous | F | 74 | 12 | 14 | 0.98 | 0.00 | ** |
| Diabetic | M | 63 | 6 | 70 | 1.17 | 0.31 | 0.00 |
| SUM of ulcer areas | | | | | 138.81 | 80.56 | 34.80 |

*did not fully heal within 140 days
**fully healed within 4 weeks

The study was conducted as an open label, non-randomized, phase 1 study.

Subjects were followed until wound closure, or if the wound did not close fully, the subjects were treated for 16 weeks. Subjects were followed up weekly during the treatment period, at which time photographs were taken. Wound measurements were done with Image J software (NIH).

Stimulation Treatment

The apparatus in accordance with some applications of the present invention is a computerized electrotherapy system based on specially designed software which generates an electrical signal characterized by randomly varying pulse/peak parameters.

The apparatus is intended for home use. It is a self-contained unit with two electrodes placed around the wound. The apparatus is operated three times daily for thirty minutes each session.

At treatment initiation, the software automatically calibrates the treatment amplitude to be attained during the treatment session. Each treatment session lasts for 30 minutes in which the device generates a balanced low intensity current described elsewhere herein (maximum current density; 0.32 mA/cm2 r.m.s.) with a net zero DC.

Results Obtained in Example 1

Reference is again made Table A, which presents the overall results of study described in Example 1.

As shown in Table A, at 4 weeks there was an average improvement of 36.20% in wound size as compared to at enrollment. Five out of the thirty-four wounds healed completely by four weeks (14.70%). Age, gender, wound type and duration of wound had no statistical effect on the outcome.

At 12 weeks there was an average improvement of 74.92% in wound size as compared to the baseline. As compared to the improvement at week 4, there was a further 56.80% improvement in wound size. A further 12 wounds healed completely between weeks 4 and 12 (35.30%). In total, by week 12, 17 wounds healed completely (50%).

At 16 weeks a further 3 wounds closed completely. The average size of the remaining wounds was 1.82 $cm^2$ a reduction of 55% from initiation.

Another 6 wounds healed completely by week 20 (17.65).

Out of 34 wounds 23 were completely closed within 140 days. Average time to fully heal for this group was 79 days. In the Diabetic Foot Ulcers group there were fourteen males and nine females. In the Venous Leg Ulcers group there were four males and seven females. There was no difference in the effect of gender on the results of the study.

No adverse events or safety issues with the device were reported during the study.

Figure 15:
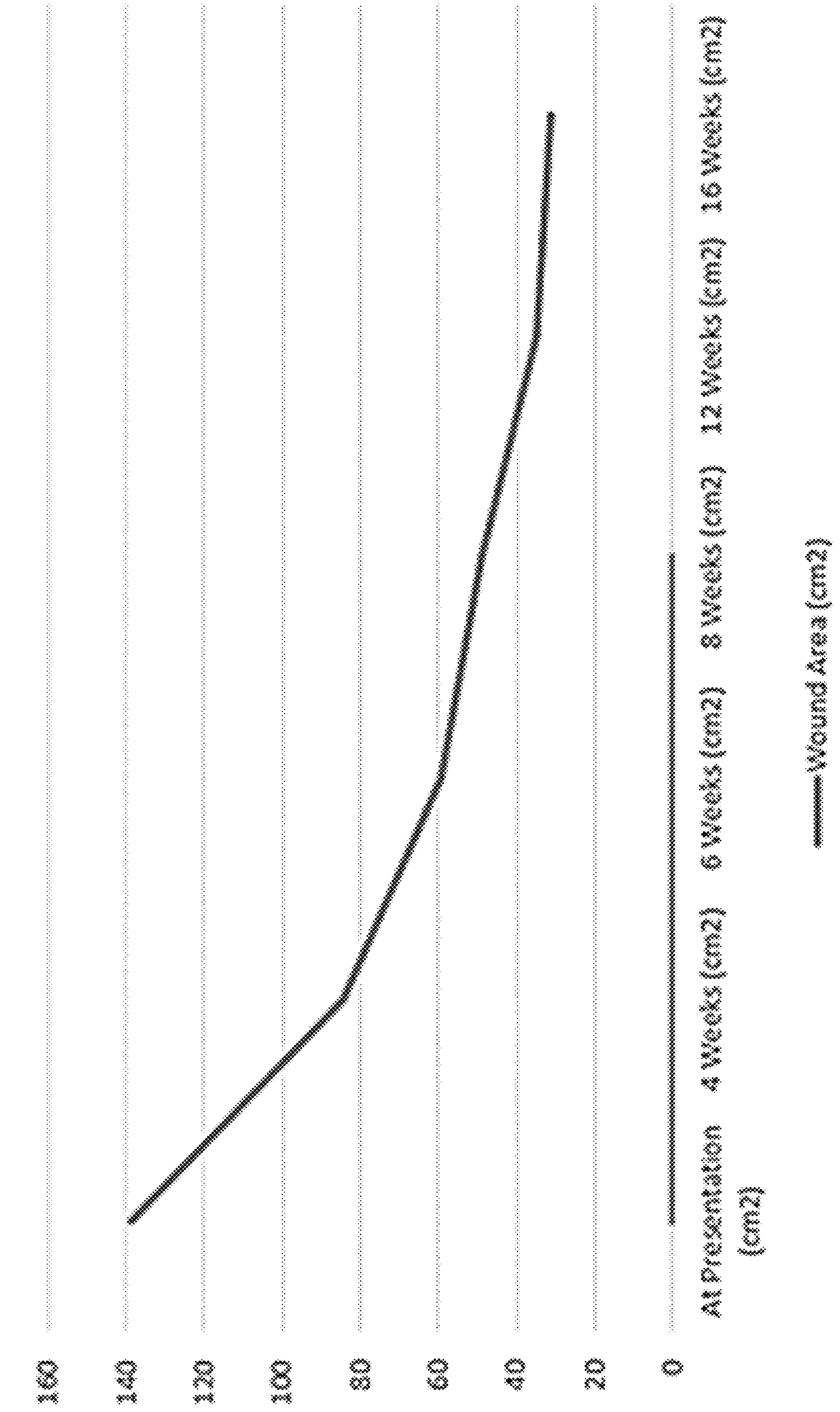
FIG. 15 is a chart representative of total wound area measured on time basis in response to treatment with the apparatus and method in accordance with some embodiments of the present invention.

As may be seen in FIG. 15, Chart I is representative of total wound area measured on time basis in response to treatment with the apparatus and method in accordance with some applications of the present invention.

Example 2

In a set of experiments, the effect of the apparatus and techniques described herein on chronic wound healing and tissue oxygenation was examined.

Methods in Example 2

Obtaining Subject Population:

This study included 8 patients (2F;6M), all elderly (74.5±5.8 years), with poor arterial circulation (TcPO2=29.1 mmHg±9.6), except one (37 years; TcPO2=64 mmHg). All had ulcers «not healing» of the lower limbs (2 post traumatic; 1 pressure sore; 1 third degree burns; 2 venous; 2 diabetic). Surface average 12.5 cm2±9.8, PushTool average 11.5±2.6 pt.

Stimulation Treatment

Low intensity current in microamperes range, 3 times daily 30 minutes each, electrodes placed on healthy intact skin in the vicinity of wounds edges. All ulcers were treated with dressings made in accordance with the best practice. The varied electrical signal was applied as described herein.

Results Obtained in Example 2

The percentage of wound surface reduction and improvement of granulation and epithelization were assessed (measured by Push Tool 3.0 system). Results: Three patients achieved complete wound closure up to 40 days. Two patients discharged from the study due to hospitalization for other causes. One patient suspended because she was tired of the procedure. Two patients are still in treatment. In all cases except one (virtually unchanged) we observed a statistically significant reduction of wound surface and P.T.

values (−49% and −4 pt P<0.05 respectively). The average treatment time was 35.1±17.5 days. TcPO2 after treatment increased from 29.1 mmHg±9. to 49.5 mmHg±6.7.

Reference is now made to FIGS. 4A-13D which are examples of chronic wounds in subjects (selected from Table A), prior to, during and following treatment of the subject in accordance with some applications of the present invention. As described with reference to Example 1 and listed in Table A, subjects suffering from Diabetic Foot Ulcers or Venous Leg Ulcers were treated in accordance with application of the present invention in order to effect healing of the wound.

FIGS. 4A-4D are images of a venous leg ulcer in an 84-year-old female subject having suffered from the wound for a duration of 12 months prior to initiation of treatment in accordance with some applications of the present invention. FIGS. 4A-D show the wound before, during a following treatment.

Figure 4B:
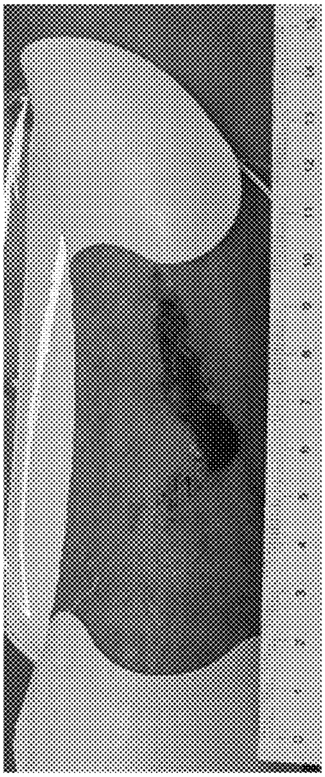
FIGS. 4A-4D, 5A-5D, 6A-6D, 7A-7D, 8A-8D, 9A-9D, 10A-10D, 11A-11D, 12A-12D and 13A-13D are examples of chronic wounds in subjects prior to, during and following treatment of the subject in accordance with some applications of the present invention.
Figure 4C:
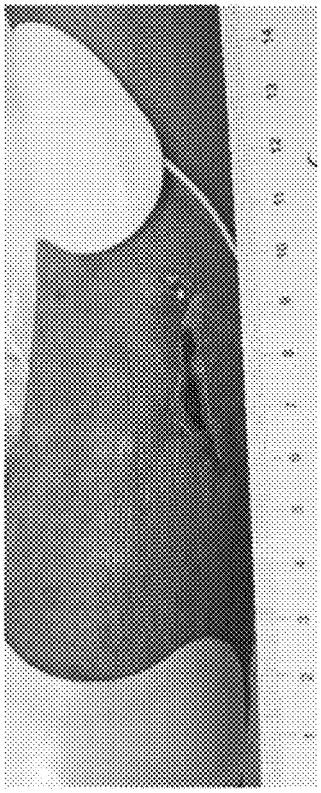
Figure 4A:
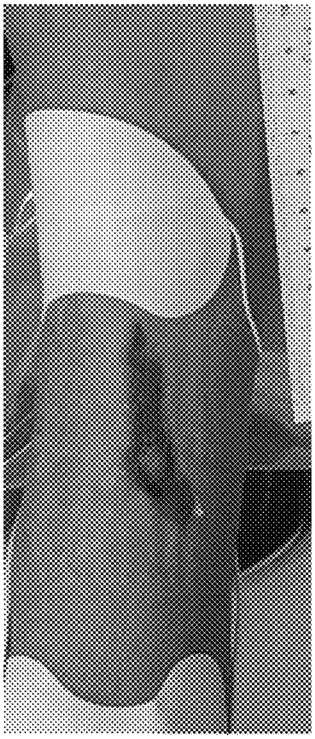

FIG. 4A shows the wound at time 0 before application of treatment.

FIG. 4B shows partial healing of the wound at 5 weeks from the beginning of treatment in accordance with some applications of the present invention.

FIG. 4C shows additional partial healing of the wound at 7 weeks from the beginning of treatment in accordance with some applications of the present invention.

Figure 4D:

FIG. 4D shows full closure of the wound at 11 weeks from the beginning of treatment in accordance with some applications of the present invention. FIG. 4D shows full closure of the wound from 4.8 cm2 to 0.0 cm2.

FIGS. 5A-5D are images of a diabetic foot ulcer in a 68-year-old female subject having suffered from the wound for a duration of 3 months prior to initiation of treatment in accordance with some applications of the present invention. FIGS. 5A-D show the wound before, during a following treatment.

Figure 5A:
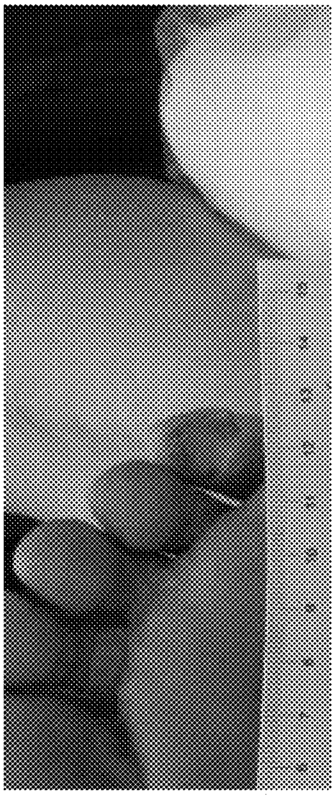

FIG. 5A shows the wound at time 0 before application of treatment.

Figure 5B:
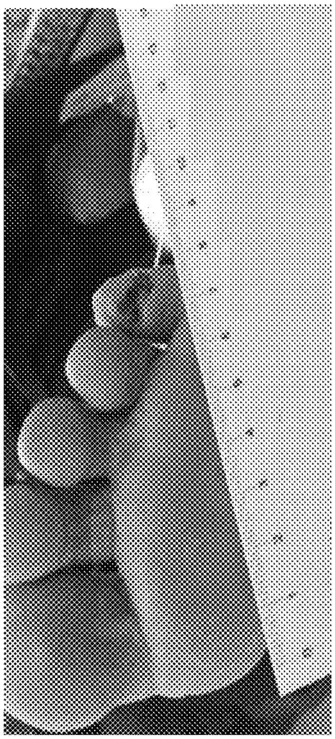

FIG. 5B shows partial healing of the wound at 4 weeks from the beginning of treatment in accordance with some applications of the present invention.

Figure 5C:
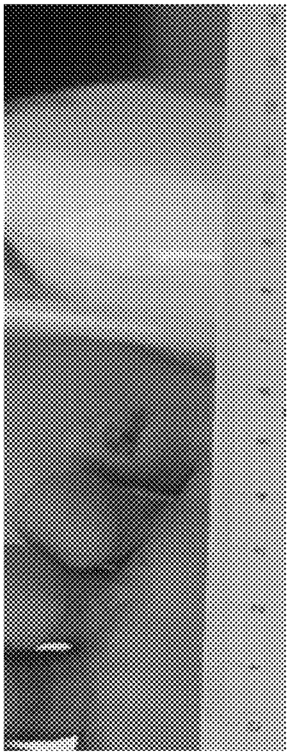

FIG. 5C shows additional partial healing of the wound at 8 weeks from the beginning of treatment in accordance with some applications of the present invention.

Figure 5D:
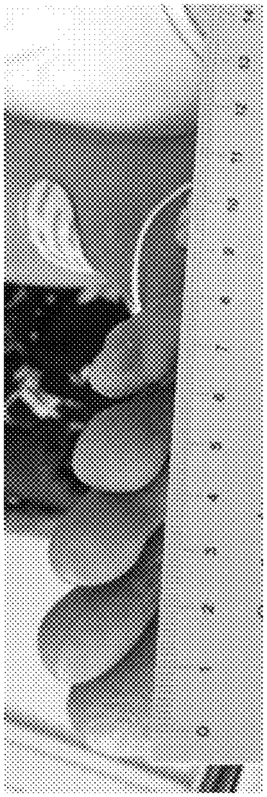

FIG. 5D shows full closure of the wound at 20 weeks from the beginning of treatment in accordance with some applications of the present invention. FIG. 5D shows full closure of the wound from 1.05 cm2 to 0.0 cm2.

FIGS. 6A-6D are images of a venous leg ulcer in an 89-year-old female subject having suffered from the wound for a duration of 4 months prior to initiation of treatment in accordance with some applications of the present invention. FIGS. 6A-D show the wound before, during a following treatment.

Figure 6A:
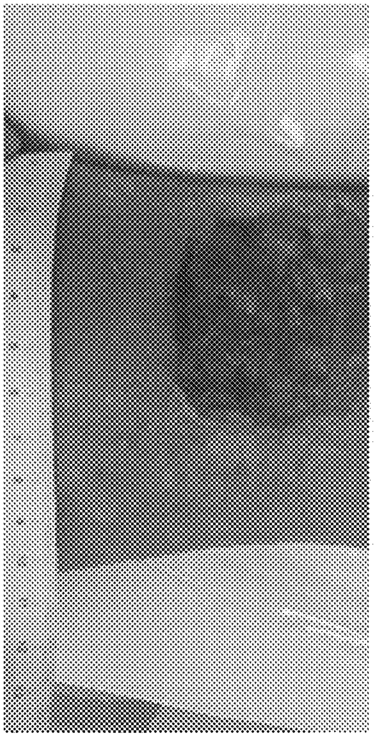

FIG. 6A shows the wound at time 0 before application of treatment.

Figure 6B:
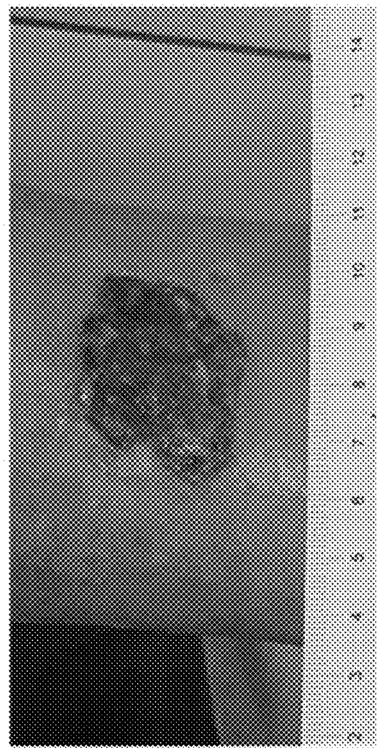

FIG. 6B shows partial healing of the wound at 2 weeks from the beginning of treatment in accordance with some applications of the present invention.

Figure 6C:
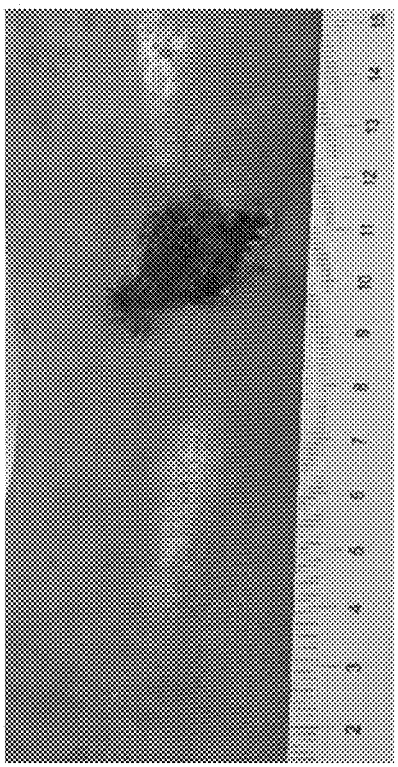

FIG. 6C shows additional partial healing of the wound at 8 weeks from the beginning of treatment in accordance with some applications of the present invention.

Figure 6D:
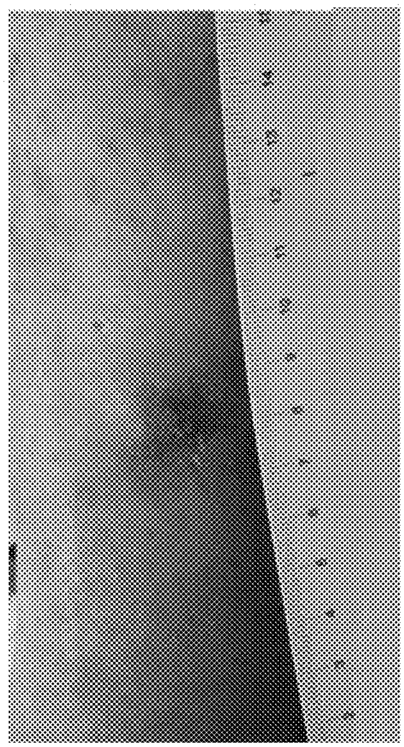

FIG. 6D shows full closure of the wound at 15 weeks from the beginning of treatment in accordance with some applications of the present invention. FIG. 6D shows full closure of the wound from 21.22 cm2 to 0.0 cm2.

FIGS. 7A-7D are images of a venous leg ulcer in a 92-year-old female subject having suffered from the wound for a duration of 17 months prior to initiation of treatment in accordance with some applications of the present invention. FIGS. 7A-D show the wound before, during a following treatment.

Figure 7A:
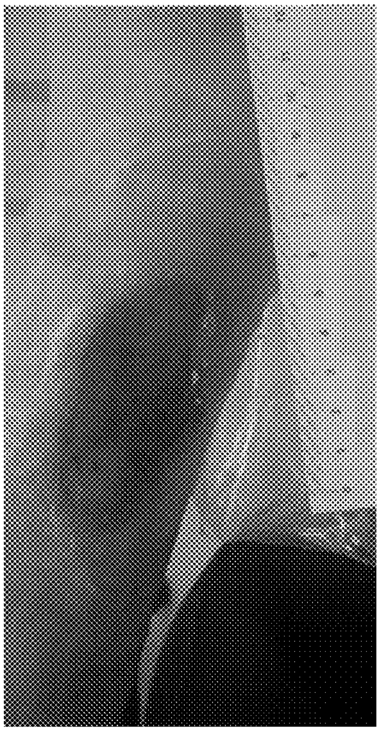

FIG. 7A shows the wound at time 0 before application of treatment.

Figure 7B:
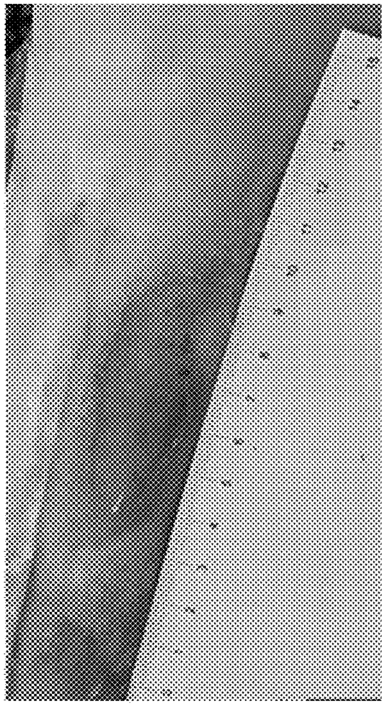

FIG. 7B shows partial healing of the wound at 3 weeks from the beginning of treatment in accordance with some applications of the present invention.

Figure 7C:
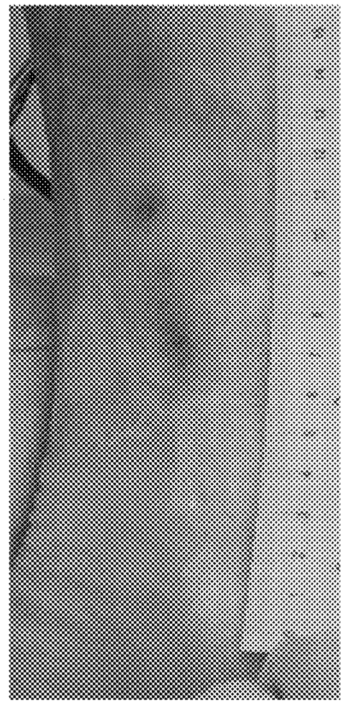

FIG. 7C shows additional partial healing of the wound at 8 weeks from the beginning of treatment in accordance with some applications of the present invention.

Figure 7D:
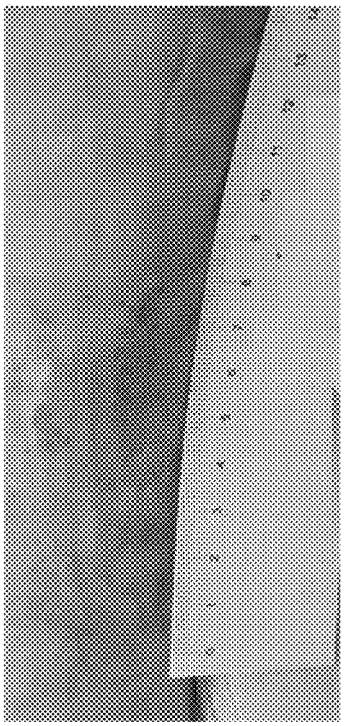

FIG. 7D shows full closure of the wound at 10 weeks from the beginning of treatment in accordance with some applications of the present invention. FIG. 7D shows full closure of the wound from 14.67 cm2 to 0.0 cm2.

FIGS. 8A-8D are images of a diabetic foot ulcer in a 77-year-old female subject having suffered from the wound for a duration of 12 months prior to initiation of treatment in accordance with some applications of the present invention. FIGS. 8A-D show the wound before, during a following treatment.

Figure 8A:
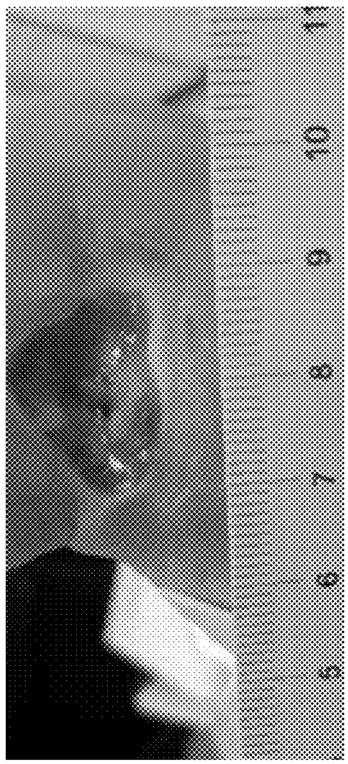

FIG. 8A shows the wound prior to initiation of a treatment session, in accordance with some applications of the present invention.

Figure 8B:
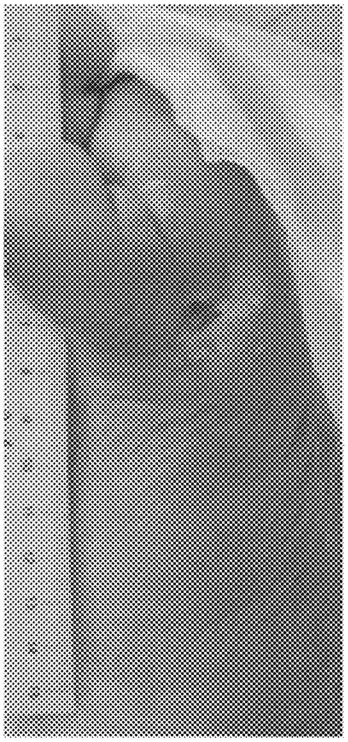

FIG. 8B shows partial healing of the wound following a previous treatment session, in accordance with some applications of the present invention, and prior to re-initiating treatment, in accordance with some applications of the present invention.

Figure 8C:
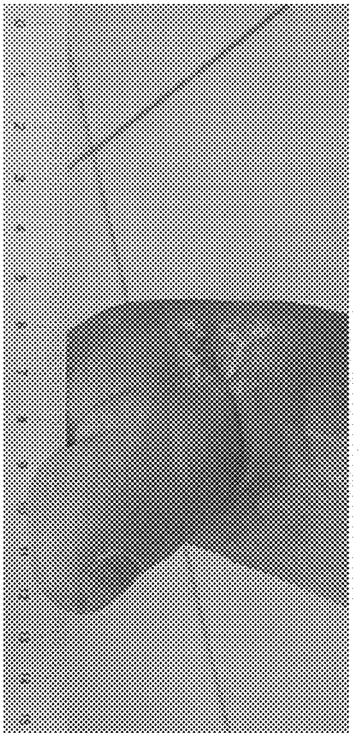

FIG. 8C shows partial healing of the wound at 6 weeks from the re-initiation of treatment in accordance with some applications of the present invention.

Figure 8D:
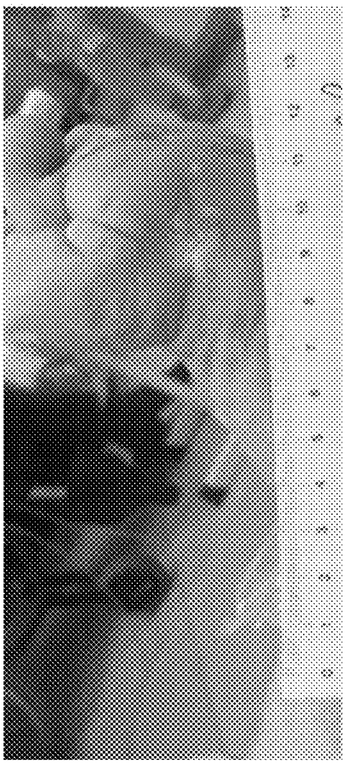

FIG. 8D shows full closure of the wound at 9 weeks from the re-initiation of treatment in accordance with some applications of the present invention. FIG. 8D shows full closure of the wound from 1.23 cm2 to 0.0 cm2.

FIGS. 9A-9D are images of an additional diabetic foot ulcer in the 77-year-old female subject of FIGS. 8A-D, having suffered from the wound for a duration of 12 months prior to initiation of treatment in accordance with some applications of the present invention. FIGS. 9A-D show the wound before, during a following treatment.

Figure 9A:
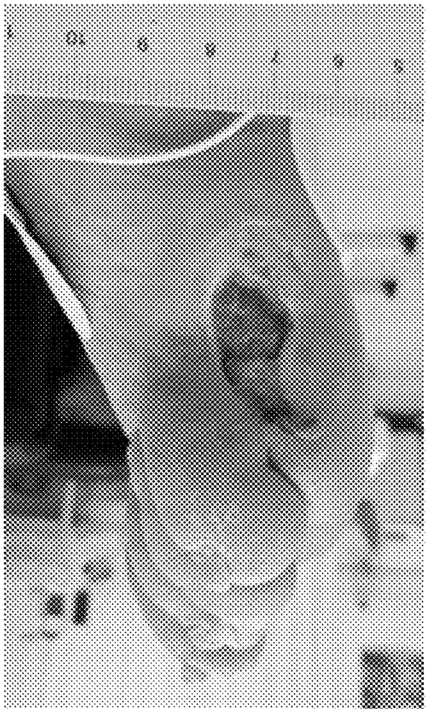

FIG. 9A shows the wound prior to initiation of a treatment session, in accordance with some applications of the present invention.

Figure 9B:
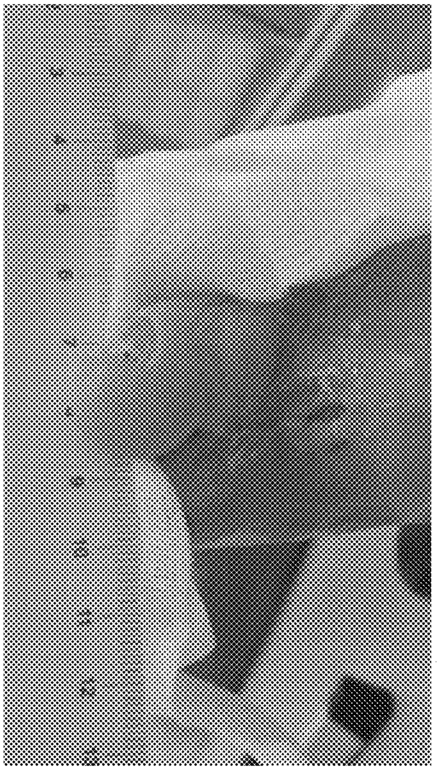

FIG. 9B shows partial healing of the wound following a previous treatment session, in accordance with some applications of the present invention, and prior to re-initiating treatment, in accordance with some applications of the present invention.

Figure 9C:
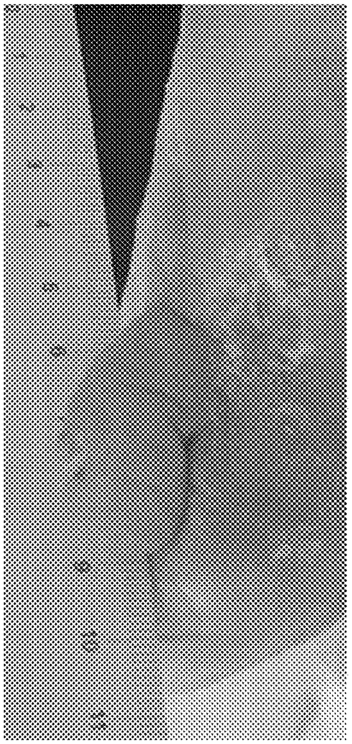

FIG. 9C shows partial healing of the wound at 6 weeks from the re-initiation of treatment in accordance with some applications of the present invention.

Figure 9D:
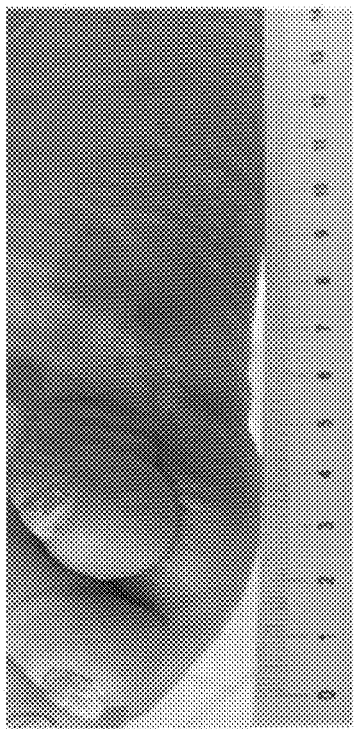

FIG. 9D shows full closure of the wound at 9 weeks from the re-initiation of treatment in accordance with some applications of the present invention. FIG. 9D shows full closure of the wound from 0.47 cm2 to 0.0 cm2.

FIGS. 10A-10D are images of a bedsore in a 92-year-old female subject having suffered from the wound for a duration of 3 months prior to initiation of treatment in accordance with some applications of the present invention. FIGS. 10A-D show the wound before, during a following treatment.

Figure 10A:
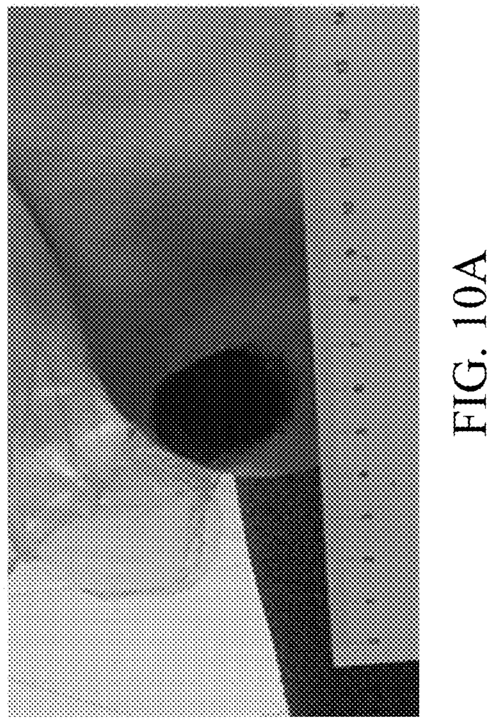

FIG. 10A shows the wound at time 0 before application of treatment.

Figure 10B:

FIG. 10B shows partial healing of the wound at 3 weeks from the beginning of treatment in accordance with some applications of the present invention.

Figure 10C:

FIG. 10C shows additional partial healing of the wound at 12 weeks from the beginning of treatment in accordance with some applications of the present invention.

Figure 10D:
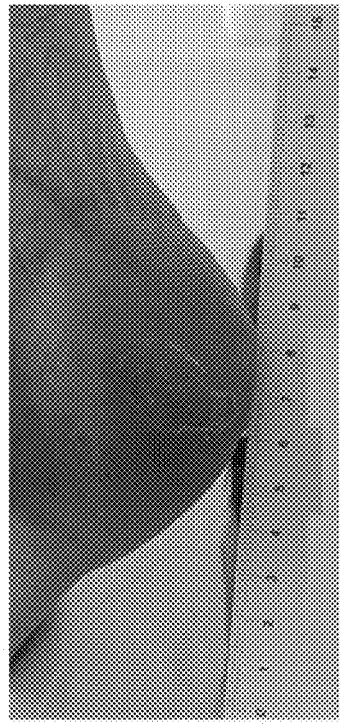

FIG. 10D shows full closure of the wound at 16 weeks from the beginning of treatment in accordance with some applications of the present invention. FIG. 10D shows full closure of the wound from 6.14 cm2 to 0.0 cm2.

FIGS. 11A-11D are images of a diabetic foot ulcer in an 86-year-old male subject having suffered from the wound for a duration of 12 months prior to initiation of treatment in accordance with some applications of the present invention. FIGS. 11A-D show the wound before, during a following treatment.

Figure 11A:
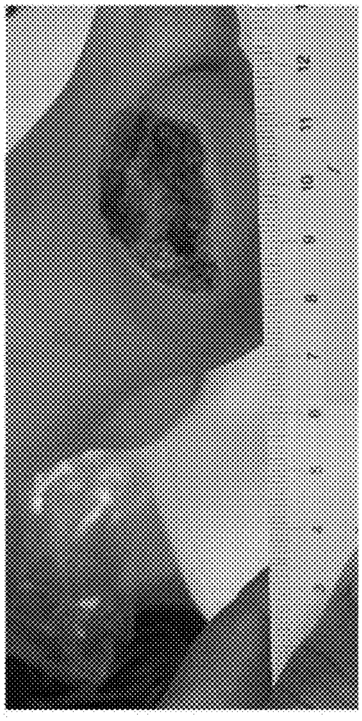

FIG. 11A shows the wound at time 0 before application of treatment.

Figure 11B:
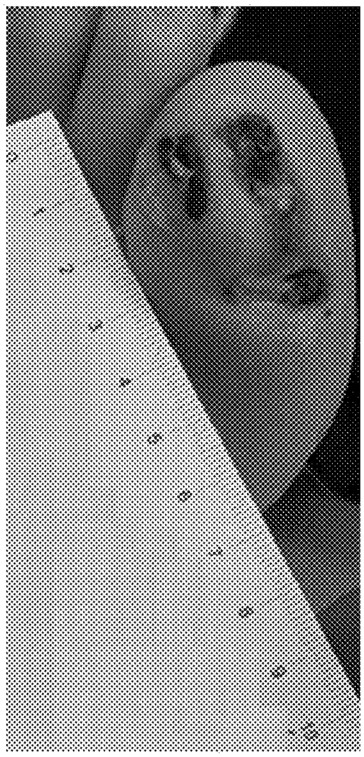

FIG. 11B shows partial healing of the wound at 4 weeks from the beginning of treatment in accordance with some applications of the present invention.

Figure 11C:
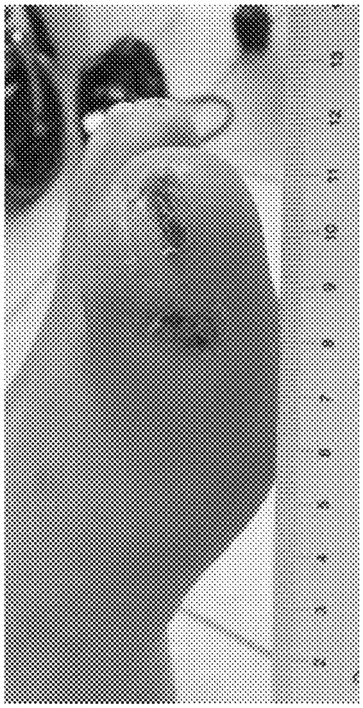

FIG. 11C shows additional partial healing of the wound at 12 weeks from the beginning of treatment in accordance with some applications of the present invention.

Figure 11D:

FIG. 11D shows further closure of the wound at 20 weeks from the beginning of treatment in accordance with some applications of the present invention. FIG. 11D shows closure of the wound from 6.07 cm2 to 0.96 cm2 (84% closure).

FIGS. 12A-12D are images of two diabetic foot ulcer in a 74-year-old female subject having suffered from the wounds for a duration of 12 months prior to initiation of treatment in accordance with some applications of the present invention. FIGS. 12A-D show the wound before, during a following treatment.

Figure 12A:
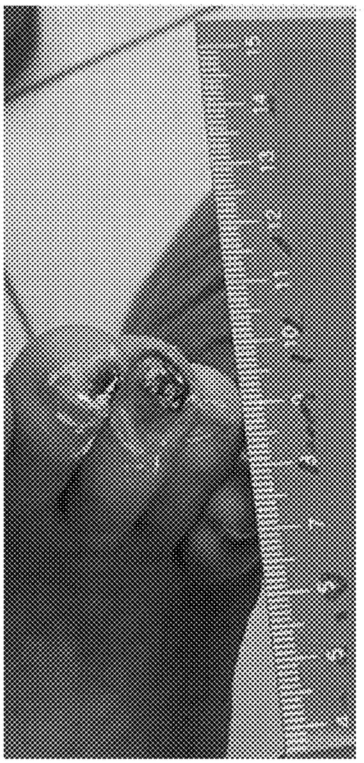

FIG. 12A shows the wound at time 0 before application of treatment.

Figure 12B:
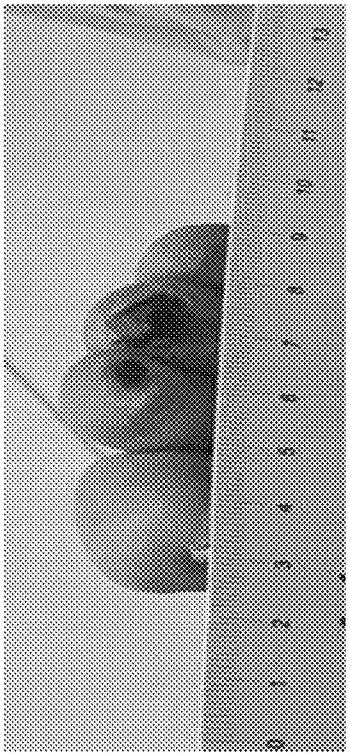

FIG. 12B shows partial healing of the wounds at 5 weeks from the beginning of treatment in accordance with some applications of the present invention.

Figure 12C:
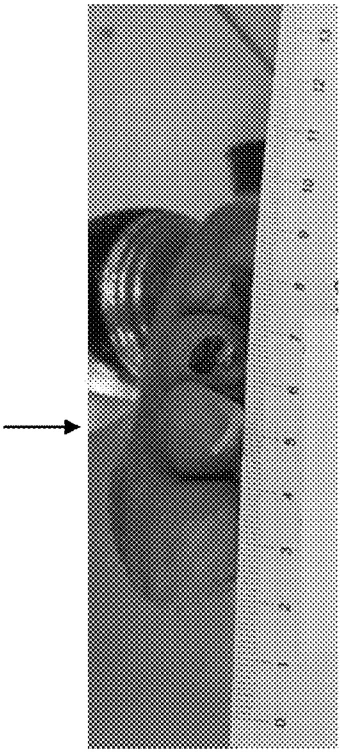

FIG. 12C shows full closure of one of the wounds (indicated by the arrow) and additional partial healing of the one of the wounds at 10 weeks from the beginning of treatment in accordance with some applications of the present invention.

Figure 12D:
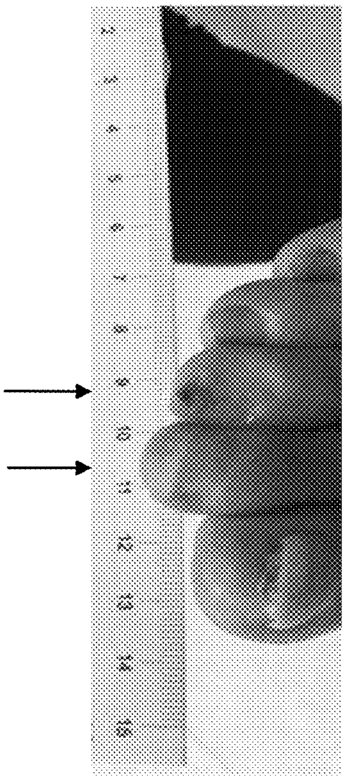

FIG. 12D shows full closure of both wounds (indicted by the arrows) at 18 weeks from the beginning of treatment in accordance with some applications of the present invention. FIG. 12D shows full closure of both wound from 1.35 cm2 to 0.0 cm2, and 1.01 to 0.0 cm2.

FIGS. 13A-13D are images of a diabetic foot ulcer in a 63-year-old male subject having suffered from the wound for a duration of 6 months prior to initiation of treatment in accordance with some applications of the present invention. FIGS. 13A-D show the wound before, during a following treatment.

Figure 13A:
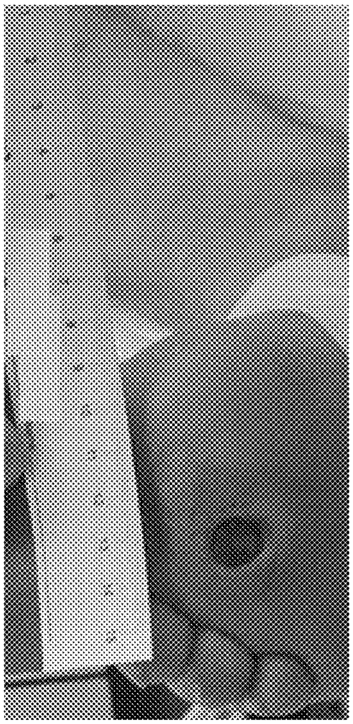

FIG. 13A shows the wound at time 0 before application of treatment.

Figure 13B:
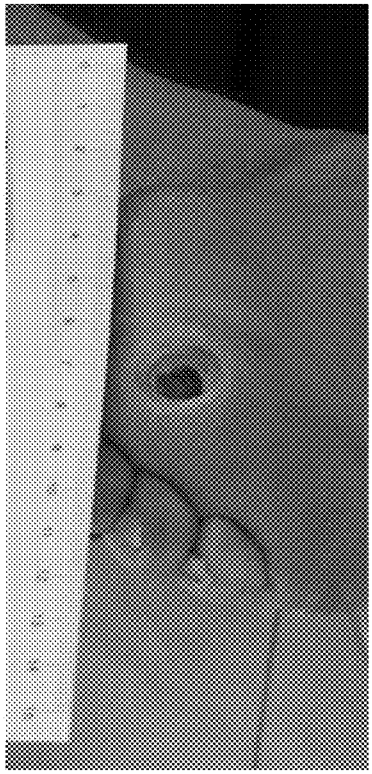

FIG. 13B shows partial healing of the wound at 2 weeks from the beginning of treatment in accordance with some applications of the present invention.

Figure 13C:
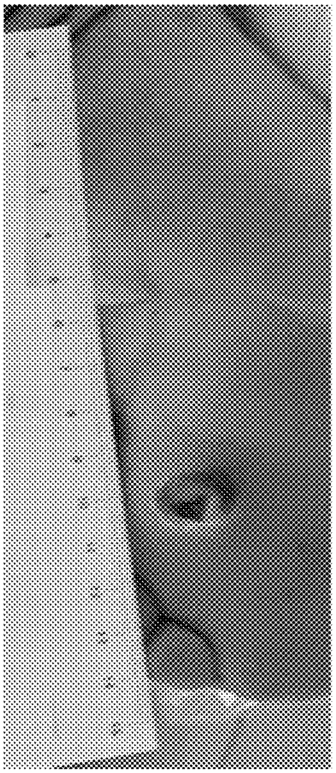

FIG. 13C shows additional partial healing of the wound at 5 weeks from the beginning of treatment in accordance with some applications of the present invention.

Figure 13D:
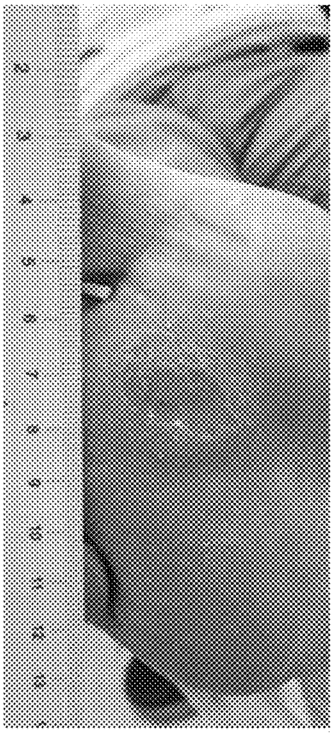

FIG. 13D shows full closure of the wound at 10 weeks from the beginning of treatment in accordance with some applications of the present invention. FIG. 13D shows full closure of the wound from 1.05 cm2 to 0.0 cm2.

Figure 14:
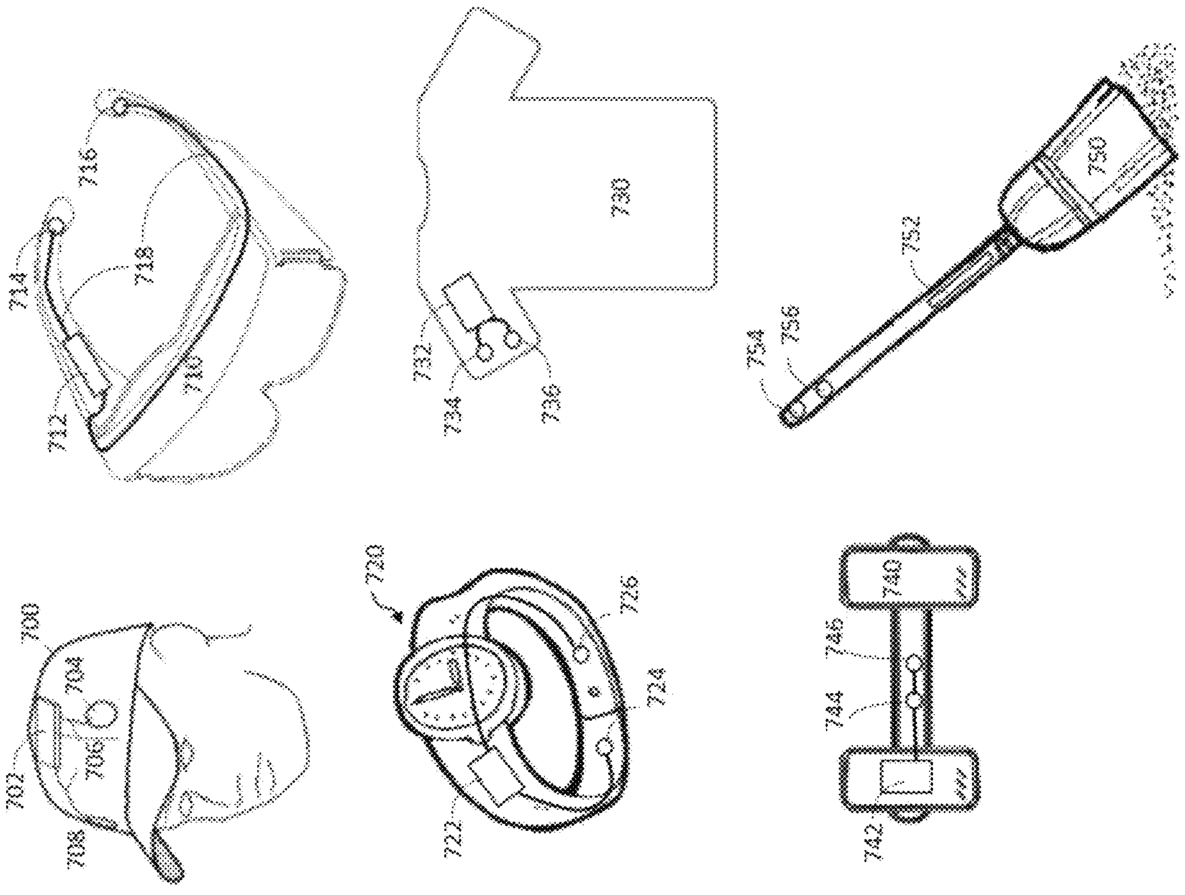
FIG. 14 is a schematic illustration a configuration of the apparatus for application of electrical stimulation therapy for use with various articles used by the subject for improving oxygen prefusion in the subject, in accordance with some applications of the present invention.

Reference is now made to FIG. 14, which is a schematic illustration a configuration of the apparatus for application of electrical stimulation therapy for use with various articles used by the subject for improving oxygen prefusion in the subject, in accordance with some applications of the present invention. Following are examples of possible placement of electrodes distant to the wound on electrode assembly articles, such as wearable and/or graspable articles. For example, the electrodes are placed distal to the wound in a wearable article, such as clothing, clothing accessories, shoes, wristbands, and the like. FIG. 14, shows schematic illustrations of articles comprising electrodes and an electrical signal generator for wound treatment. A headwear article 700, such as a hat, a cap, or the like, may have an electrode assembly incorporated into a headband of headwear article 700, such as electrodes 704 and 708 at on the inner surface of the headband of headwear article 700, adjacent to the skin of the temples of the subject. The assembly comprises electrical leads 706 embedded in headwear article 700 structure, and electrically connected to both electrodes 704 and 708 at one end of each electrical lead 706 and an electrical signal generator 702 electrically connected at the other end of electrical leads 706. A securing element, such as the headband of headwear article 700 keeps electrodes 704 and 708 firmly connected with the skin of the subject. An advantage of incorporating electrical signal generator 702 and electrode assembly in headwear article 700 is that the patient may be treated while performing other tasks, such as walking.

An eyeglasses frame 710, may have an electrode assembly incorporated into a arms of eyeglasses frame 710, such as electrodes 714 and 716 at on the inner surface of the end of each arm, adjacent to the skin behind the ears of the subject. The assembly comprises electrical leads 718 embedded in eyeglasses frame 710 structure, and electrically connected to both electrodes 714 and 716 at one end of each electrical lead 718 and an electrical signal generator 712 electrically connected at the other end of electrical leads 718. Electrical signal generator 712 may be embedded into one arm of eyeglasses frame 710. A securing element, such as the arms of eyeglasses frame 710 keeps electrodes 714 and 716 firmly connected with the skin of the subject. An advantage of incorporating electrical signal generator 712 and electrode assembly in eyeglasses frame 710 is that the patient may be treated while performing other tasks, such as reading.

A wristwatch 720, may have an electrode assembly incorporated into a wristband of wristwatch 720, such as electrodes 724 and 726 at on the inner surface of the wristband, adjacent to the skin of the wrist of the subject. The assembly comprises electrical leads embedded in the wristband, and electrically connected to both electrodes 724 and 726 at one end of each lead and an electrical signal generator 722 electrically connected at the other end of the leads. Electrical signal generator 722 may be embedded into the wristband or the watch itself. A securing element, such as the wristband of wristwatch 720 keeps electrodes 724 and 726 firmly connected with the skin of the subject. An advantage of incorporating electrical signal generator 722 and electrode assembly in wristwatch 720 is that the patient may be treated while performing other tasks.

An undershirt 730, may have an electrode assembly incorporated into an arm of undershirt 730, such as electrodes 734 and 736 at on the inner surface of the arm, adjacent to the skin of the upper arm of the subject. The assembly comprises electrical leads embedded in the arm, and electrically connected to both electrodes 734 and 736 at one end of each lead and an electrical signal generator 732 electrically connected at the other end of the leads. Electrical signal generator 732 may be embedded into the arm of undershirt 730. A securing element, such as the arms of undershirt 730 keeps electrodes 734 and 736 firmly connected with the skin of the subject. An advantage of incorporating electrical signal generator 732 and electrode assembly in undershirt 730 is that the patient may be treated while performing other tasks.

A barbell 740, may have an electrode assembly incorporated into the bar of barbell 740, such as electrodes 744 and 746 at on the outer surface of the bar, adjacent to the skin of the hand of the subject holding the bar. The assembly comprises electrical leads embedded in the bar, and electrically connected to both electrodes 744 and 746 at one end of each lead and an electrical signal generator 742 electrically connected at the other end of the leads. Electrical signal generator 742 may be embedded into the bar or the weights of barbell 740. A securing element, such as the hands of the subject keeps electrodes 744 and 746 firmly connected with the skin of the subject. An advantage of incorporating electrical signal generator and electrode assembly in barbell 740 is that the patient may perform fitness training while being treated.

A broom 750, may have an electrode assembly incorporated into the handle of broom 750, such as electrodes 754 and 756 at on the outer surface of the handle, adjacent to the skin of the hand of the subject holding the handle. The assembly comprises electrical leads embedded in the handle, and electrically connected to both electrodes 754 and 756 at one end of each lead and an electrical signal generator 752 electrically connected at the other end of the leads. Electrical signal generator 752 may be embedded into the handle of broom 750. A securing element, such as the hands of the subject keeps electrodes 754 and 756 firmly connected with the skin of the subject. An advantage of incorporating electrical signal generator 752 and electrode assembly in broom 750 is that the patient may be treated while performing other tasks, such as cleaning.

Optionally electrode assemblies are placed in medical bandages, adhesive bandages, and the like. For example, the electrodes are patch electrodes adhesively connected to the skin of a patient, and the electrical signal generator is integrated into the patch. In this example, the securing element is the adhesive of the patch. For example, the electrical signal generator and electrodes are integrated into an elastic bandage, such as used for sports injuries, and the elastic bandage is applied to a joint of the patient such that the electrodes at one end of the adhesive bandage touch the skin of the patient and the adhesive bandage is the securing element contain an electrical signal generator and the leads. Similarly, an electrical signal generator, leads and electrodes may be incorporated into a strap, a belt, a medical bandage, a spring, an elastic cord, an elastic webbing, an elastic bandage, an adhesive bandage, an adhesive patch, and the like. Optionally, these articles are incorporated into wearable articles, such as clothing, inner clothing, clothing accessories, and the like.

The two or more electrodes described article are connected by a substrate of the article, such as the substrate of an electrode assembly. The substrate may have a stiffness of greater than $1\times10^{-7}$ $Nm^2$, such as the stiffness of a cotton cloth, linen cloth, and the like. The substrate may have a stiffness of greater than $10\times10^{-7}$ $Nm^2$, such as the stiffness of a patch electrode comprising two or more electrode elements, an elastic bandage, and the like. Optionally, the substrate may have a stiffness of greater than $100\times10^{-7}$ $Nm^2$, such as the stiffness of a headband, a wrist strap of a wristwatch, a headband of a hat, and the like. Optionally, the substrate may have a stiffness of greater than $1\times10^{-4}$ $Nm^2$, such as the stiffness of a bar of a barbell, a broom handle, and the like. Optionally, the substrate may have a stiffness greater than $1\times10^{-9}$ $Nm^2$. Optionally, the substrate may have a stiffness between $1\times10^{-9}$ $Nm^2$ and $1\times10^{9}$ $Nm^2$.

Some applications of the present invention may be a system, an apparatus, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the “C” programming language or similar programming languages. The computer readable program instructions may execute entirely on the user’s computer, partly on the user’s computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for electrical stimulation of tissue comprising:

an electrical stimulator comprising at least one electrode configured to be placed in contact with skin of a subject;

a signal generator configured to provide an electrical signal of a pulsed electrical current to pass through the subject through the at least one electrode, wherein the electrical signal comprises a plurality of series of pulses; and a control processor configured to continuously randomly vary signal parameters including: (i) an energy value of each of said pulses, and (ii) a duration of each of said pulses;

wherein said plurality of series of pulses comprises:

at least one first series of pulses, comprising at least 250 positive pulses and at least 250 negative pulses per second, said pulses of the at least one first series having (i) the energy value of 0.5-13 microjoule, (ii) the duration between 0.25 ms and 0.5 ms, and (iii) an average energy value of 1-4 microjoule; and at least one second series of pulses, comprising at least 100 positive pulses and at least 100 negative pulses per second, said pulses of the at least one second series having (i) the energy value of 0.005-7 microjoule, (ii) the duration between 0.05 ms and 0.25 ms, and (iii) the average energy value of 0.02-1 microjoule; and wherein the control processor is configured to mix the at least one first series and the at least one second series at random intervals between the pulses thereof.

2. The apparatus according to claim 1, wherein said electrical signal comprises an equal number of positive polarity pulses and negative polarity pulses, and wherein a total electrical charge delivered by said electrical signal to said subject is equal to zero.

3. The apparatus according to claim 1, wherein said series of pulses comprises discrete pulses.

4. The apparatus according to claim 1, wherein each of said pulses has a waveform selected from the group consisting of: sinusoidal, square, triangle, and a combination thereof; and wherein the electrical signal is a stochastic AC signal.

5. The apparatus according to claim 1, wherein said control processor is configured to repeat a pattern of said signal parameters no more than once within a predetermined time duration, wherein said predetermined time duration is 0.2 seconds.

6. The apparatus according to claim 1, wherein the at least one electrode is configured to be placed in contact with skin of the subject in the vicinity of a treatment site wherein the treatment site is one of a list consisting of: a wound in the skin, a location suffering from impaired oxygenation, and upstream of afferent axons leading to the spinal cord.

7. The apparatus according to claim 1, wherein said plurality of series of pulses further comprises at least one third series of pulses comprising at least 150 positive pulses and at least 150 negative pulses per second, said pulses of the at least one third series having (i) the energy value of 1-20 microjoules, (ii) the duration between 0.5 ms and 1 ms, and (iii) an average energy value of 2-10 microjoules.

8. A method for electrical stimulation of a group of nerves, the method comprising:

placing at least one electrode in contact with skin of a subject, in a vicinity of a wound in the skin;

applying an electrical signal of a pulsed electrical current to pass through the subject through the at least one electrode, wherein the electrical signal comprises a plurality of series of pulses; and continuously randomly varying signal parameters including: (i) an energy value of each of said pulses, and (ii) a duration of each of said pulses;

wherein said plurality of series of pulses comprises:

at least one first series of pulses, comprising at least 250 positive pulses and at least 250 negative pulses per second, said pulses of the at least one first series having (i) the energy value of 0.5-13 microjoule, (ii) the duration between 0.25 ms and 0.5 ms, and (iii) an average energy value of 1-4 microjoule; and at least one second series of pulses, comprising at least 100 positive pulses and at least 100 negative pulses per second, said pulses of the at least one second series having (i) the energy value of 0.005-7 microjoule, (ii) the duration between 0.05 ms and 0.25 ms, and (iii) the average energy value of 0.02-1 microjoule; and mixing the at least one first series and the at least one second series at random intervals between the pulses thereof.

9. The method according to claim 8, wherein said electrical signal comprises an equal number of positive polarity pulses and negative polarity pulses, and wherein a total electrical charge delivered by said electrical signal to said subject is equal to zero.

10. The method according to claim 8, wherein said series of pulses comprises discrete pulses.

11. The method according to claim 8, wherein each of said pulses has a waveform selected from the group consisting of: sinusoidal, square, triangle, and a combination thereof; and wherein the electrical signal is a stochastic AC signal.

12. The method according to claim 8, comprising repeating a pattern of said signal parameters no more than once within a predetermined time duration, wherein said predetermined time duration is 0.2 seconds.

13. The method according to claim 8, wherein said placing the at least one electrode in contact with the skin of the subject is performed upstream of afferent axons leading to the spinal cord.

14. The method according to claim 8, wherein said plurality of series of pulses further comprises at least one third series of pulses comprising at least 150 positive pulses and at least 150 negative pulses per second, said pulses of the at least one third series having (i) the energy value of 1-20 microjoules, (ii) the duration between 0.5 ms and 1 ms, and (iii) an average energy value of 2-10 microjoules.

* * * * *